United States Patent
Elton et al.

(10) Patent No.: US 8,322,756 B2
(45) Date of Patent: *Dec. 4, 2012

(54) DISCONNECTABLE CONNECTOR ASSEMBLY

(75) Inventors: Darren Elton, Southampton (GB); Richard Martin, Swindon (GB)

(73) Assignee: Pall Corporation, Port Washington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/104,098

(22) Filed: May 10, 2011

(65) Prior Publication Data

US 2011/0209785 A1  Sep. 1, 2011

Related U.S. Application Data

(63) Continuation of application No. 12/169,884, filed on Jul. 9, 2008, now Pat. No. 7,959,192.

(51) Int. Cl.
*A61M 39/00* (2006.01)
(52) U.S. Cl. ........ 285/376; 604/256; 604/905; 604/323; 137/614.03
(58) Field of Classification Search .................... 285/376; 604/256, 905, 323; 137/614.03
See application file for complete search history.

(56) References Cited

U.S. PATENT DOCUMENTS

| | | | |
|---|---|---|---|
| 1,968,421 | A | 1/1931 | Proctor |
| 2,457,251 | A | 12/1948 | Main, Jr. |
| 2,471,237 | A | 5/1949 | Pasturczak |
| 3,583,667 | A | 6/1971 | Amneus |
| 4,499,932 | A | 2/1985 | Perigo et al. |
| 5,628,726 | A | 5/1997 | Cotter |
| 5,762,646 | A | 6/1998 | Cotter |
| 5,845,943 | A | 12/1998 | Ramacier, Jr. et al. |
| 6,036,675 | A | 3/2000 | Thorne et al. |
| 6,041,805 | A | 3/2000 | Gydesen et al. |
| 6,070,623 | A | 6/2000 | Aneas |
| 6,626,884 | B1 | 9/2003 | Dillon et al. |
| 7,090,191 | B2 | 8/2006 | Matkovich et al. |
| 7,153,296 | B2 | 12/2006 | Mitchell |
| 7,252,308 | B2 | 8/2007 | Thilly |
| 2002/0093192 | A1 | 7/2002 | Matkovich |

(Continued)

FOREIGN PATENT DOCUMENTS

WO  WO 93/14688  8/1993

(Continued)

OTHER PUBLICATIONS

European Search Report, Application No. 09164370.0, dated Oct. 5, 2012.

*Primary Examiner* — David E Bochna
(74) *Attorney, Agent, or Firm* — Leydig, Voit & Mayer, Ltd.

(57) ABSTRACT

A disconnectable connector assembly is provided, including a first fitting having a movable stem therein, the stem being movable from one end toward the other end of the first fitting; a valve releasably attached to the stem, the valve including legs engageable with a lip; a second fitting connected to the first fitting, the second fitting including the lip, the second fitting being in fluid communication with the stem and the first fitting when the stem is in a first position, and wherein fluid flow between the second fitting and the stem and the first fitting is blocked when the stem is in a second position; the first fitting being disconnectable from the second fitting after the stem has been moved and the valve is released from the stem with the legs engaged with the lip when the first and second fittings are disconnected.

19 Claims, 23 Drawing Sheets

U.S. PATENT DOCUMENTS

| | | |
|---|---|---|
| 2002/0129858 A1 | 9/2002 | Meyer et al. |
| 2003/0173380 A1 | 9/2003 | Gerber et al. |
| 2005/0017505 A1 | 1/2005 | Thilly |

FOREIGN PATENT DOCUMENTS

| | | |
|---|---|---|
| WO | WO 98/50105 | 11/1998 |
| WO | WO 03/090843 A1 | 11/2003 |
| WO | WO 2004/106484 | 12/2004 |

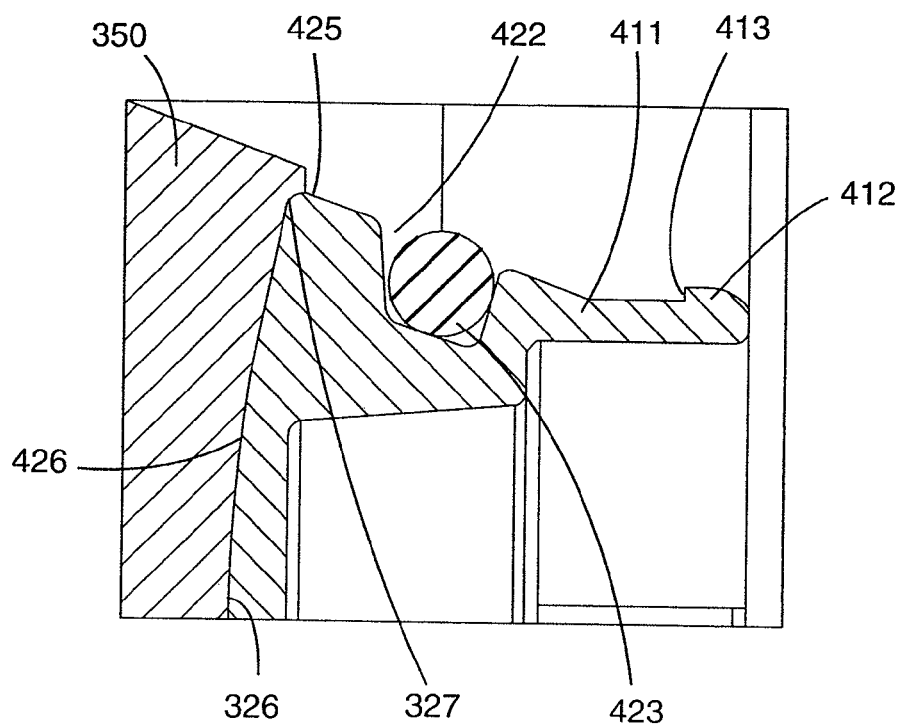
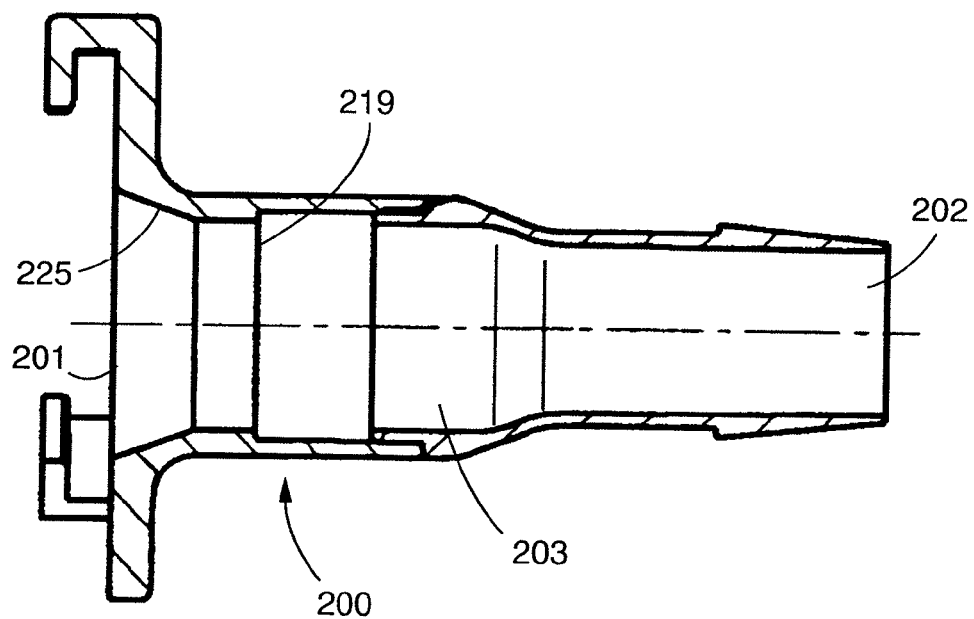

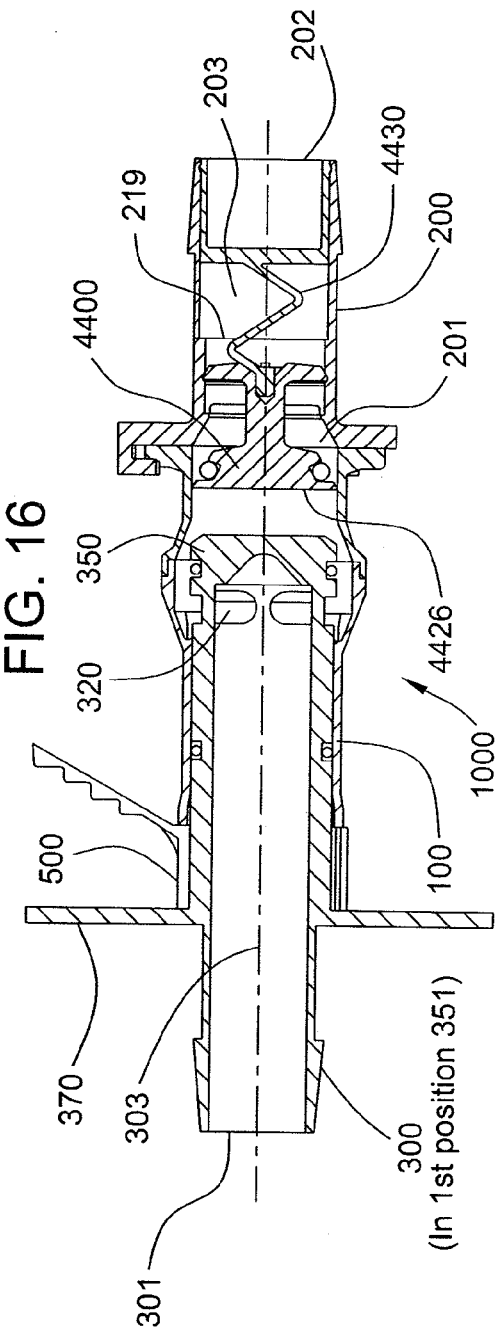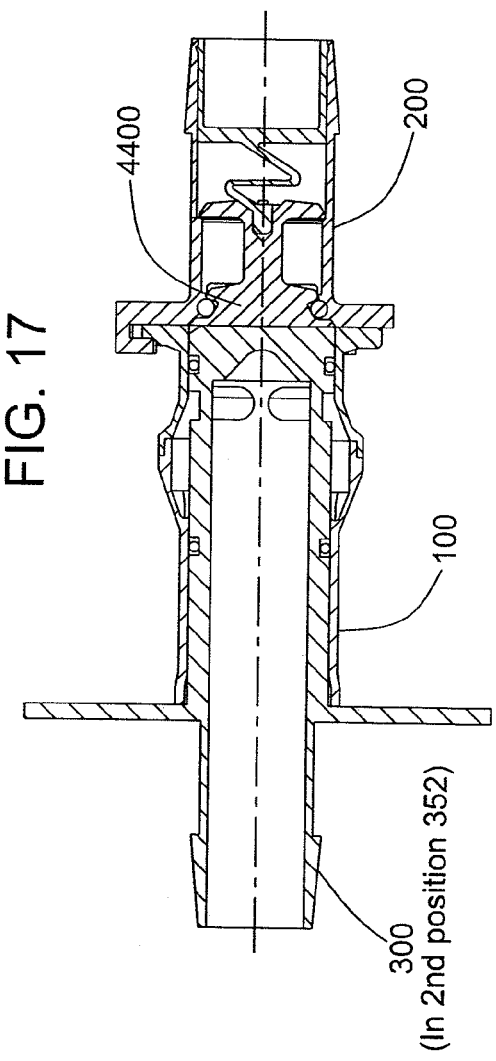

DISCONNECTABLE CONNECTOR ASSEMBLY

CROSS-REFERENCE TO RELATED APPLICATIONS

This patent application is a continuation of U.S. Patent Application No. 12/169,884, filed Jul. 9, 2008, issued as U.S. Pat. No. 7,959,192.

BACKGROUND OF THE INVENTION

Polymeric tubing is used to provide fluid communication between various components in a fluid processing system. When disconnecting components from the system, e.g., temporarily, or permanently, electronic tubing sealers and clamps are used, followed by cutting to separate the portions of tubing. This can be labor intensive, and can require the tube sealing equipment to be transported to one or more desired location.

The present invention provides for ameliorating at least some of the disadvantages of the prior art. These and other advantages of the present invention will be apparent from the description as set forth below.

BRIEF SUMMARY OF THE INVENTION

An embodiment of the invention provides a disconnectable connector assembly comprising first and second fittings, and a stem, wherein the stem is disposed in the first fitting, and is axially moveable therein from a first position to a second position, wherein the assembly allows fluid communication through the assembly when the stem is in the first position, and prevents fluid communication through the assembly when the stem is in the second position, and wherein the assembly is disconnectable, with the disconnected end of the first fitting remaining fluid tightly sealed, when the stem is in the second position.

In some embodiments, the assembly further comprises a valve that remains in the second fitting after the assembly is disconnected, and the disconnected end of the second fitting remains fluid tightly sealed.

Embodiments of the invention also comprise sets including the assemblies, and methods of using the assemblies.

BRIEF DESCRIPTION OF THE SEVERAL VIEWS OF THE DRAWING(S)

Figure 7A:
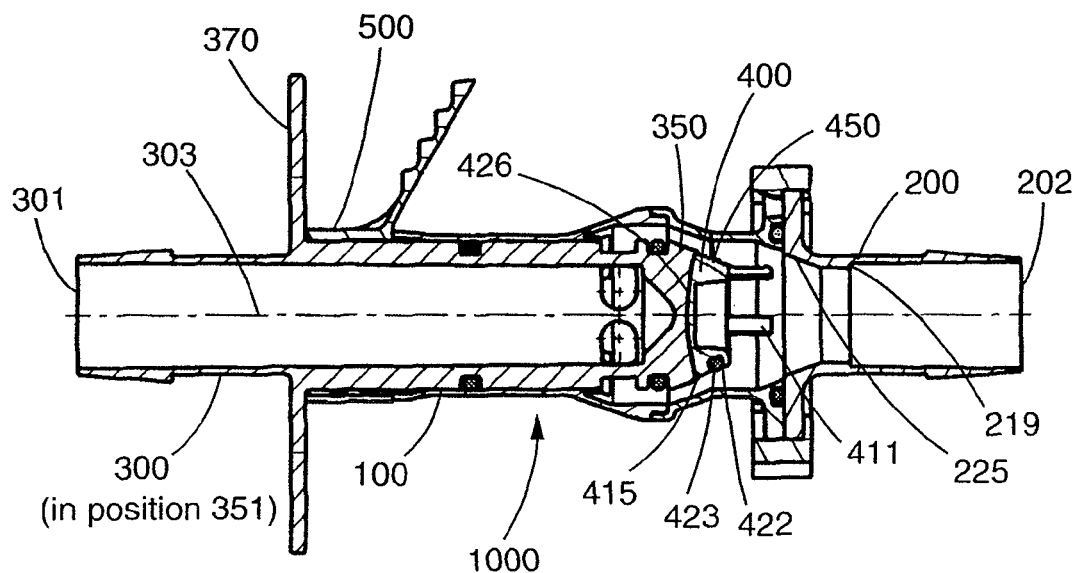
Figure 7B:
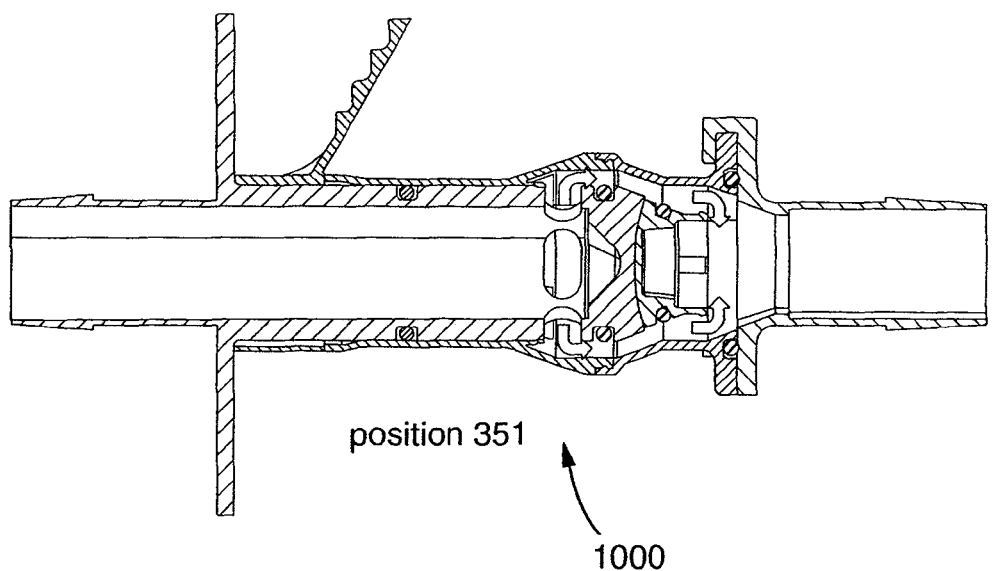

FIG. 7 shows a cross-sectional view (FIG. 7A) of another embodiment of the disconnectable connector assembly of the present invention comprising first and second fittings, and including a releasable valve attached to the stem, wherein the fittings are connected, and the stem is in the first position, allowing fluid flow through the assembly, and shows in more detail in another cross-sectional view (FIG. 7B), the fluid flow path when the stem is in the first position.

Figure 8:
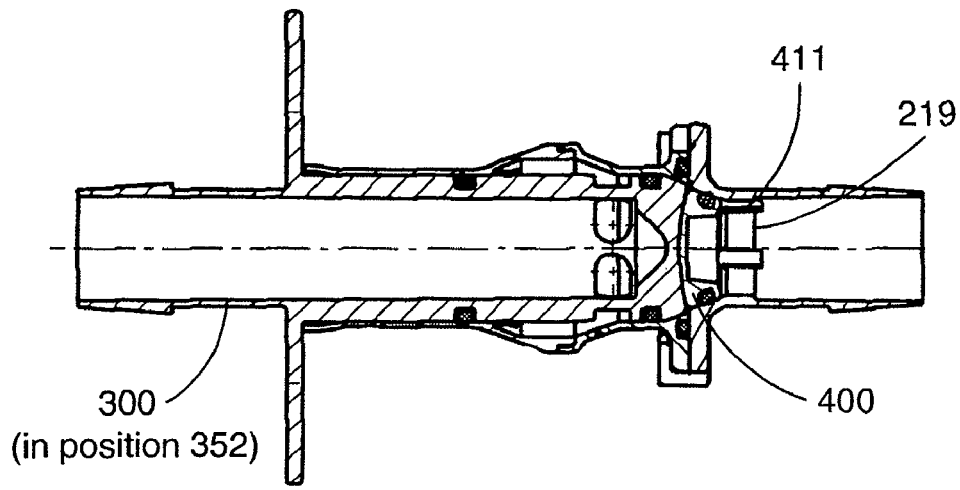

FIG. 8 is a cross-sectional view of the assembly shown in FIG. 7, wherein the stem is in the second position, and the valve is closed, preventing fluid flow through the assembly.

Figure 9:
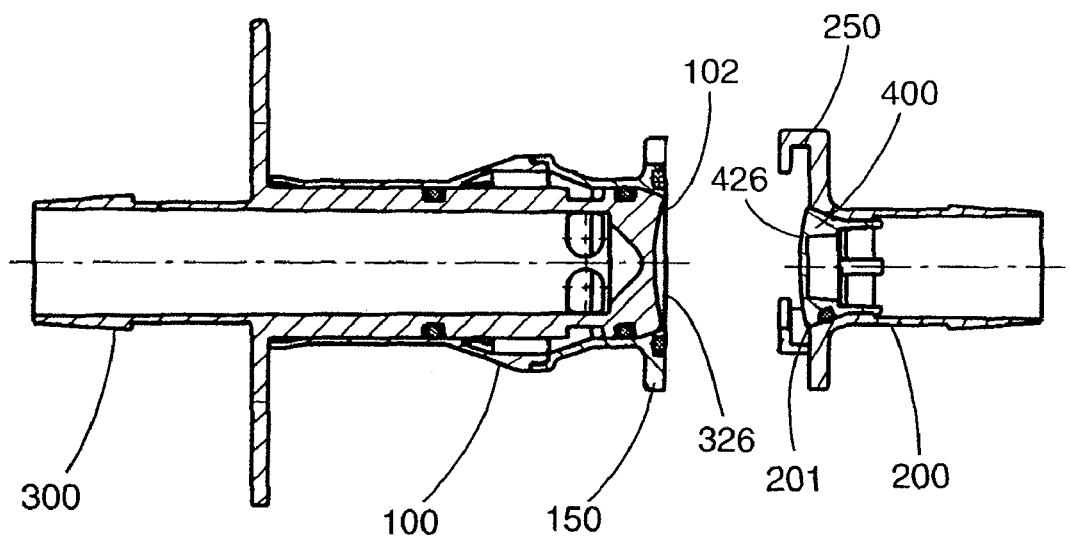

FIG. 9 is a cross-sectional view of the assembly shown in FIG. 7, after disconnection, showing separated first and second fittings, wherein the stem is in the second position, the valve has been released from the stem, and the disconnected ends of the separated first fitting and the second fitting remain closed.

Figure 10:
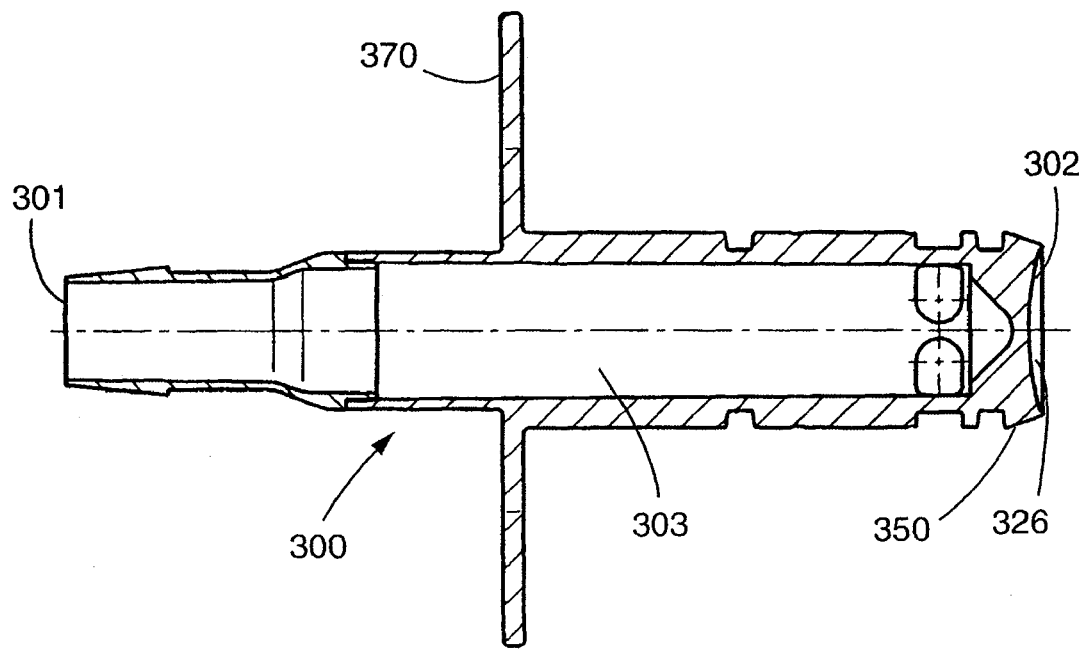

FIG. 10 shows a cross-sectional view of a stem used in the embodiment of the assembly shown in FIG. 7.

FIG. 11 shows a cross-sectional view of a portion of the head of the stem and the valve shown in FIG. 7, showing the releasable connection of the valve to the stem.

Figure 12:
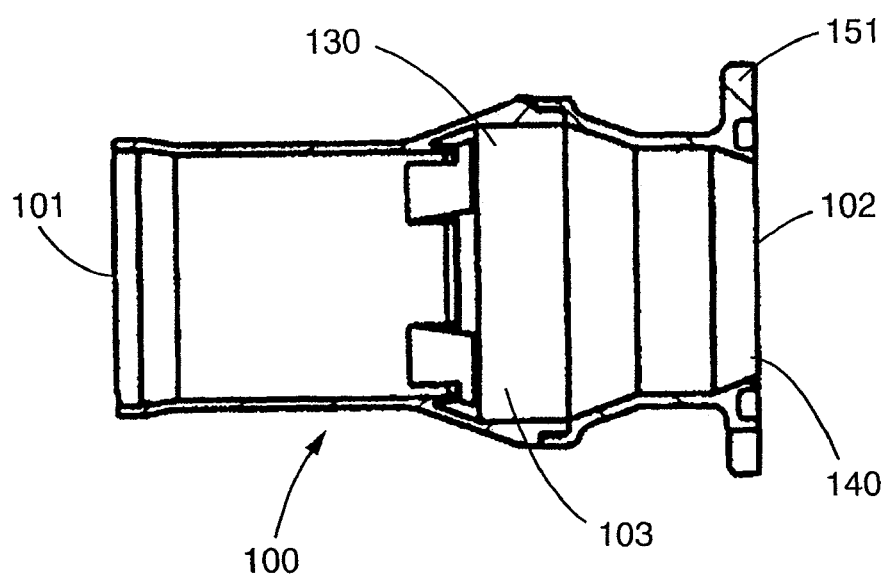

FIG. 12 shows a cross-sectional view of the first fitting used in the embodiment of the assembly shown in FIG. 7.

FIG. 13 shows a cross-sectional view of the second fitting used in the embodiment of the assembly shown in FIG. 7.

Figure 14A:
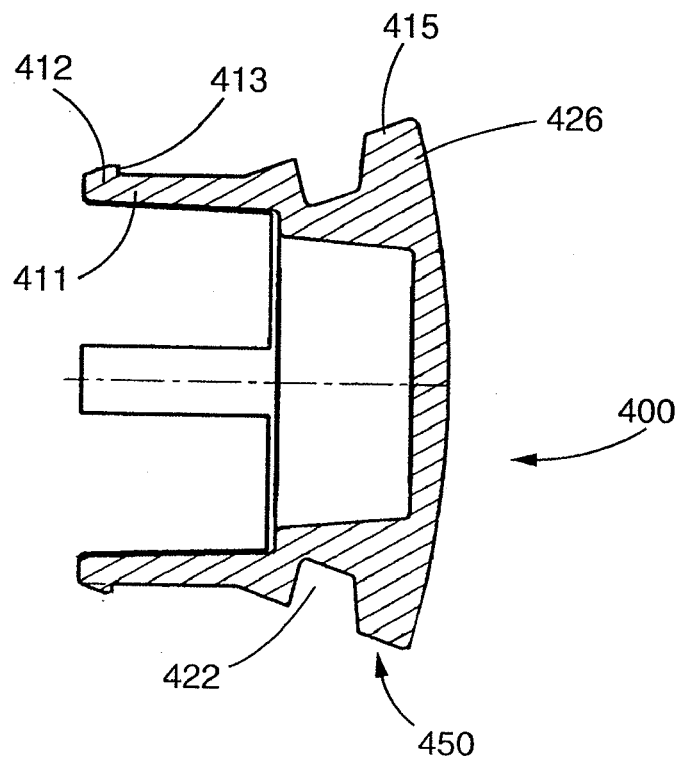
Figure 14B:
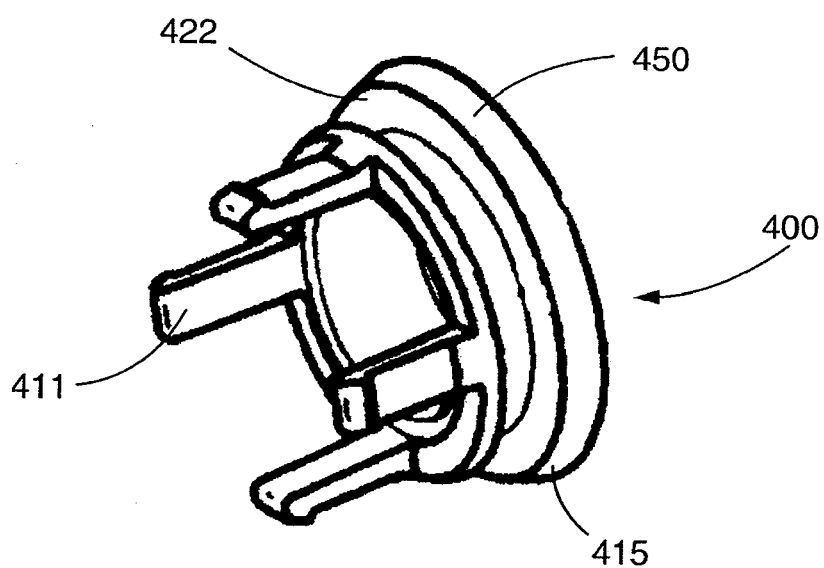
Figure 14C:
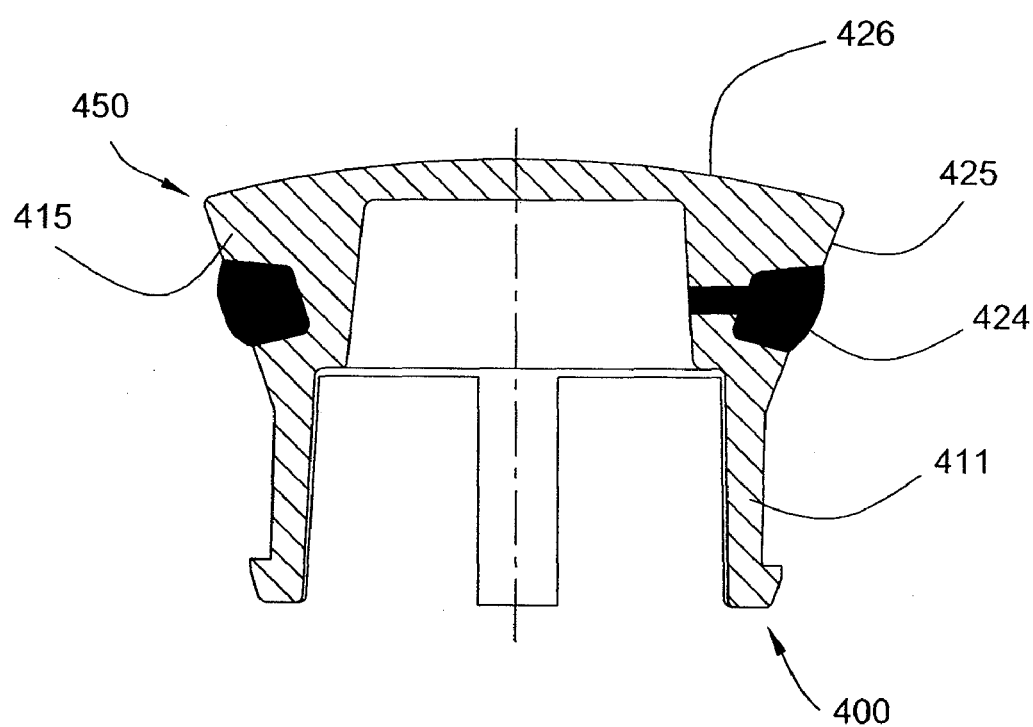

FIG. 14 shows a cross-sectional view (FIG. 14A; o-ring not shown) and a perspective view (FIG. 14B) of the valve shown in FIG. 7. FIG. 14C shows a cross-sectional view of another embodiment of the valve, wherein the valve includes a resilient portion.

Figure 15:
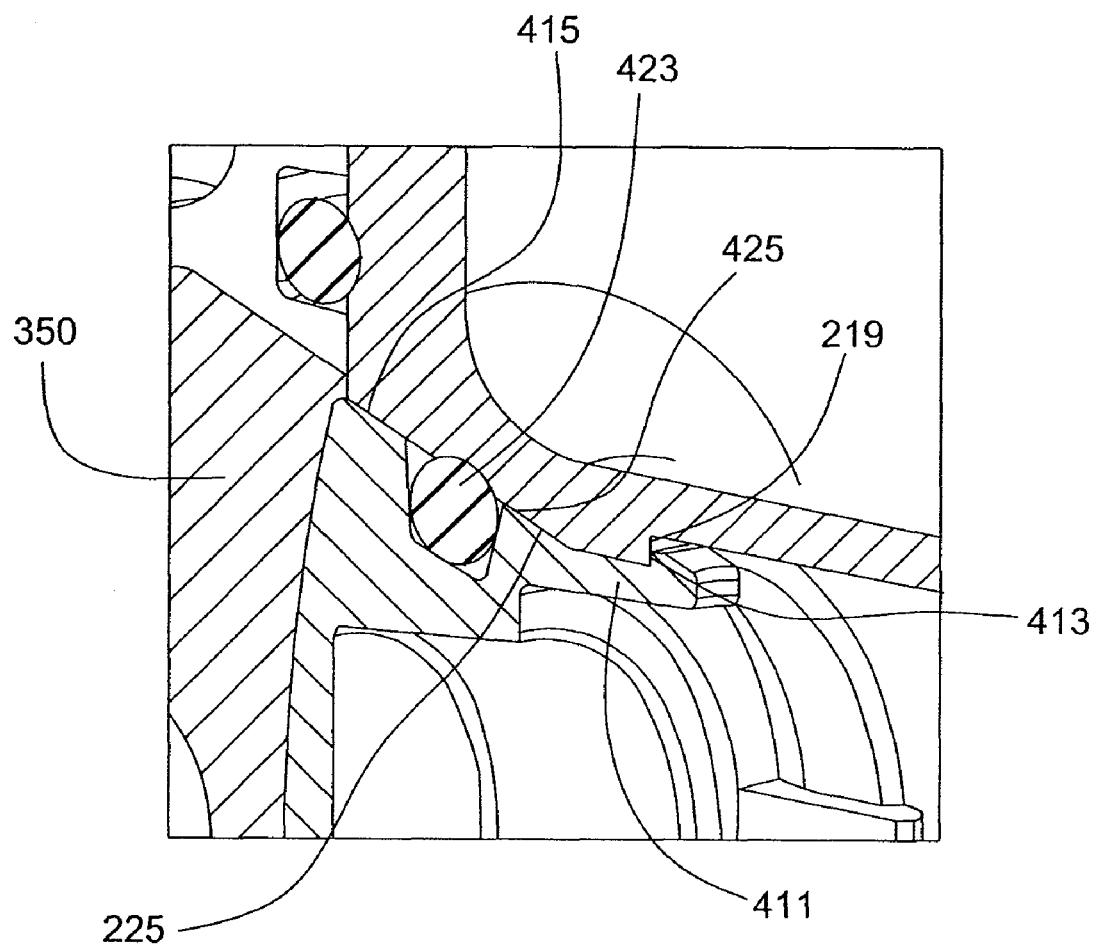

FIG. 15 shows a cross-sectional view of a portion of the second fitting with the stem in the second position, showing the engagement of the valve with the fitting.

FIG. 16 shows a cross-sectional view of another embodiment of the disconnectable connector assembly of the present invention comprising first and second fittings, and including a valve and valve guide and a spring mounted in the second fitting, wherein the valve is not attached to the stem and the valve is open, the fittings are connected, and the stem is in the first position, allowing fluid flow through the assembly.

FIG. 17 is a cross-sectional view of the assembly shown in FIG. 16, wherein the stem is in the second position, and the valve is closed, preventing fluid flow through the assembly.

Figure 18:
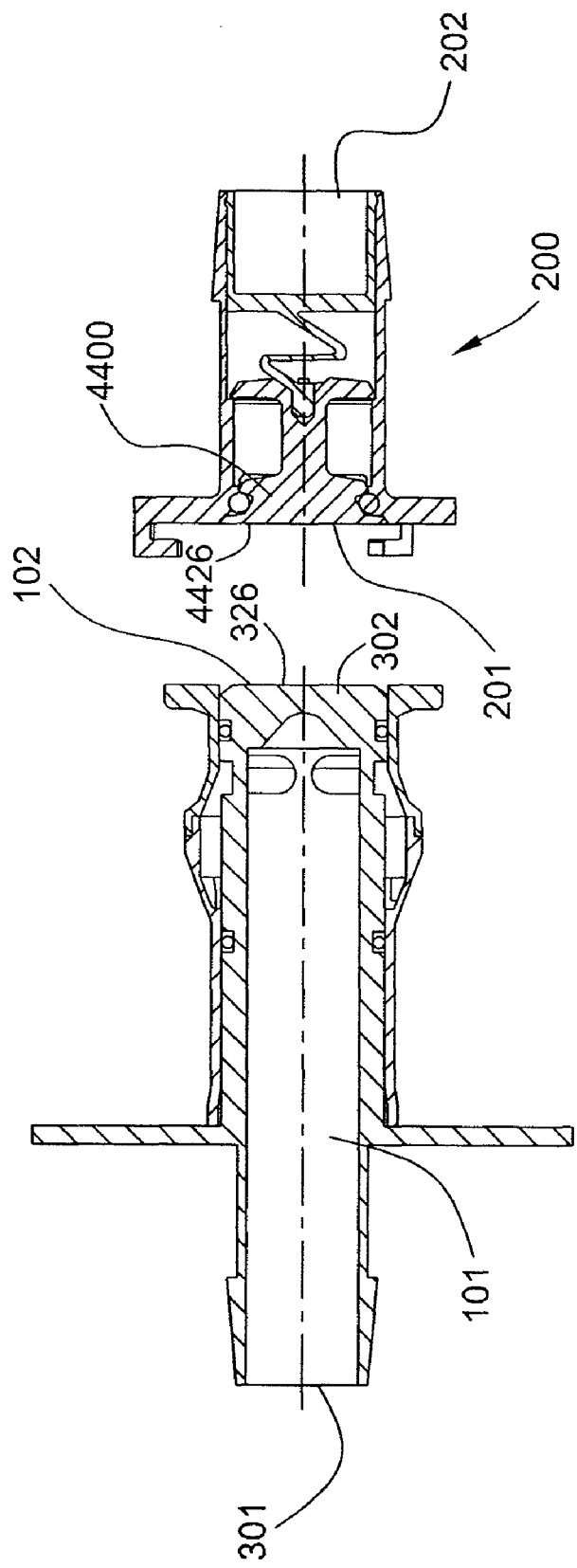

FIG. 18 is a cross-sectional view of the assembly shown in FIG. 16, after disconnection, showing separated first and second fittings, wherein the stem is in the second position, the valve has been seated in the second fitting, and the disconnected ends of the separated first and second fittings remain closed.

Figure 19:
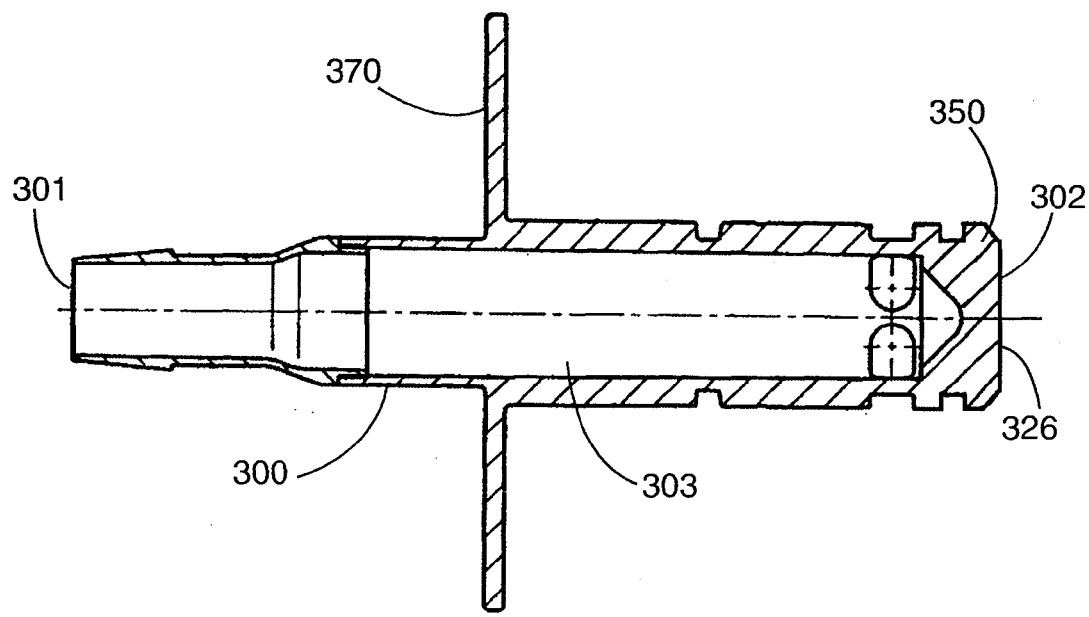

FIG. 19 shows a cross-sectional view of a stem used in the embodiment of the assembly shown in FIG. 16.

Figure 20:
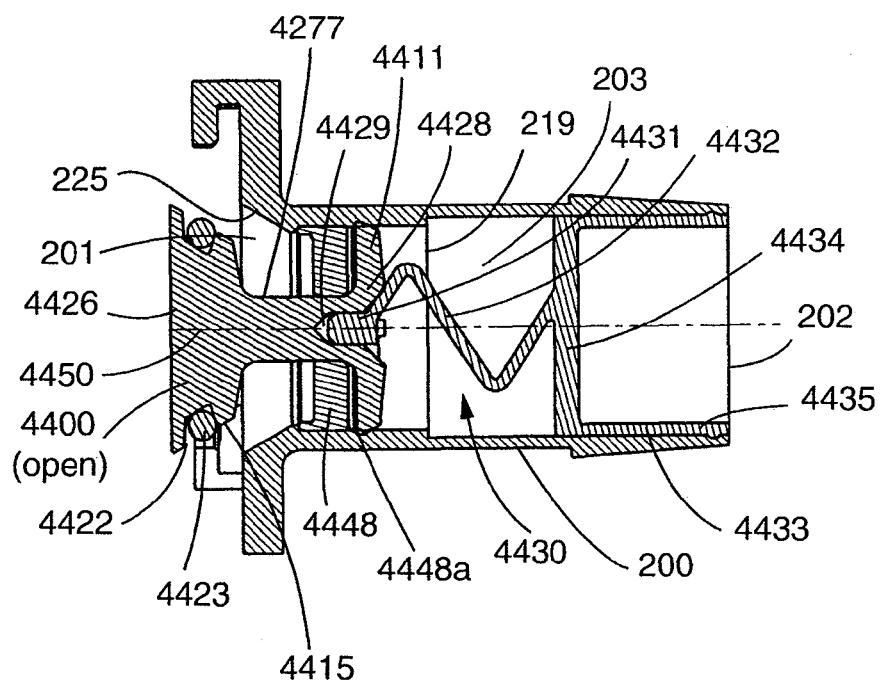

FIG. 20 shows a cross-sectional view of the second fitting shown in FIG. 16, also showing the valve, valve guide, and spring, mounted in the second fitting, when the stem is in the first position and the valve is open, the valve being retained by the valve guide.

Figure 21:
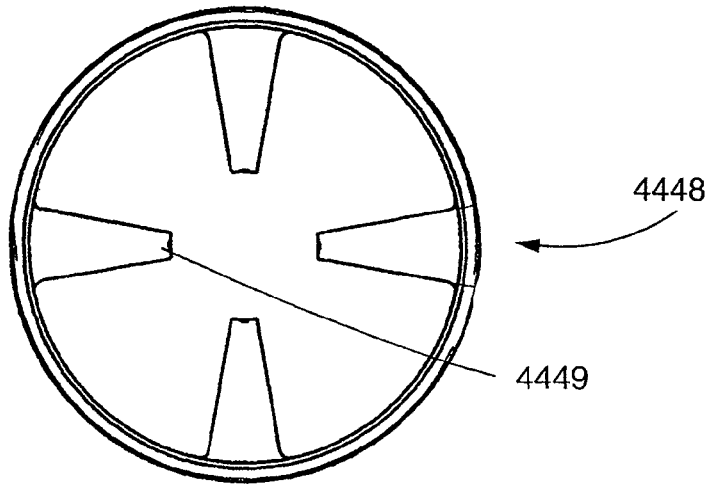

FIG. 21 shows a top view of the valve guide used in the embodiment of the assembly shown in FIG. 16.

Figure 22A:
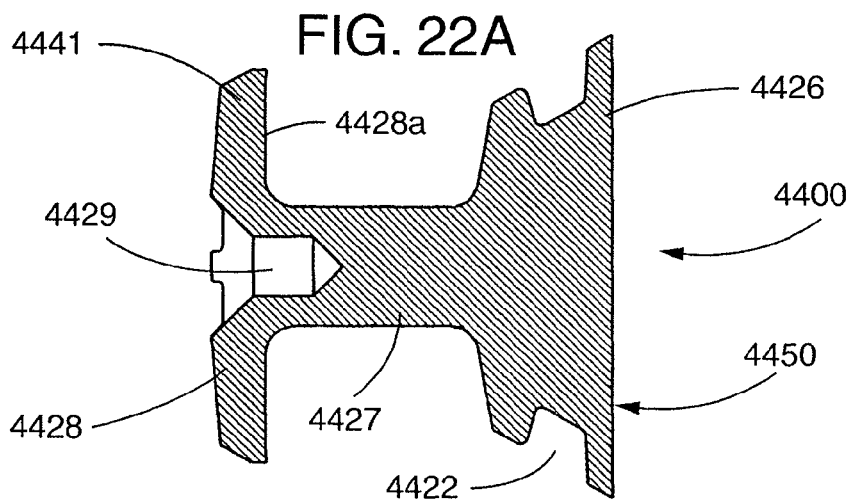
Figure 22B:
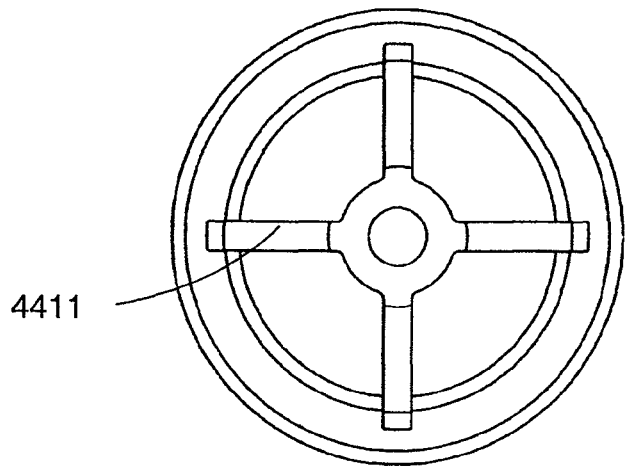

FIG. 22 shows a cross-sectional view (FIG. 22A) and a bottom view (FIG. 22B) of the valve used in the embodiment of the assembly shown in FIG. 16.

Figure 23A:
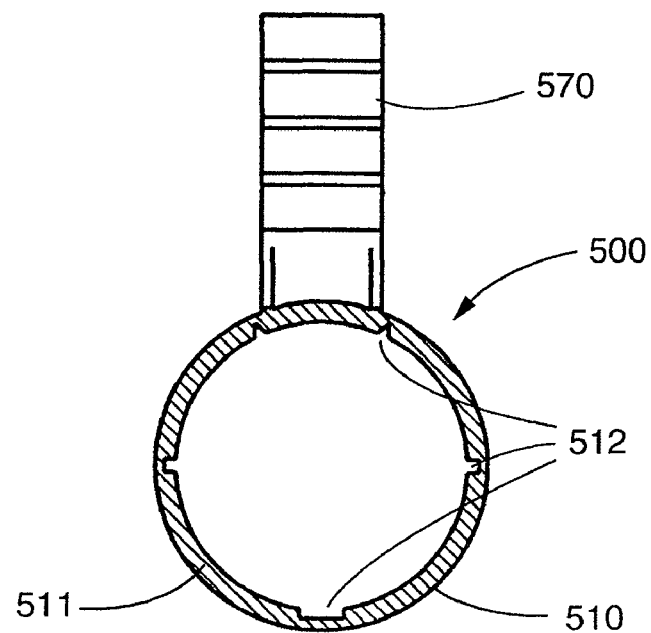
Figure 23B:
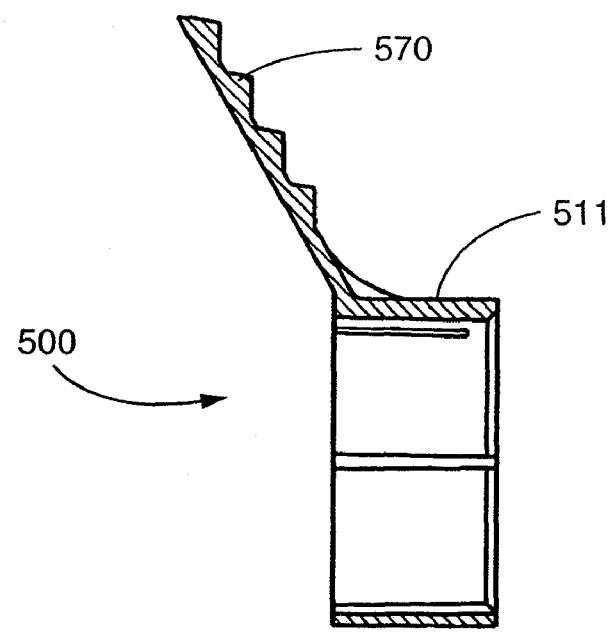

FIG. 23 shows a perspective view (FIG. 23A) and a cross-sectional view (FIG. 23B) of a lock out device, preventing movement of the stem from the first position to the second position.

Figure 24:
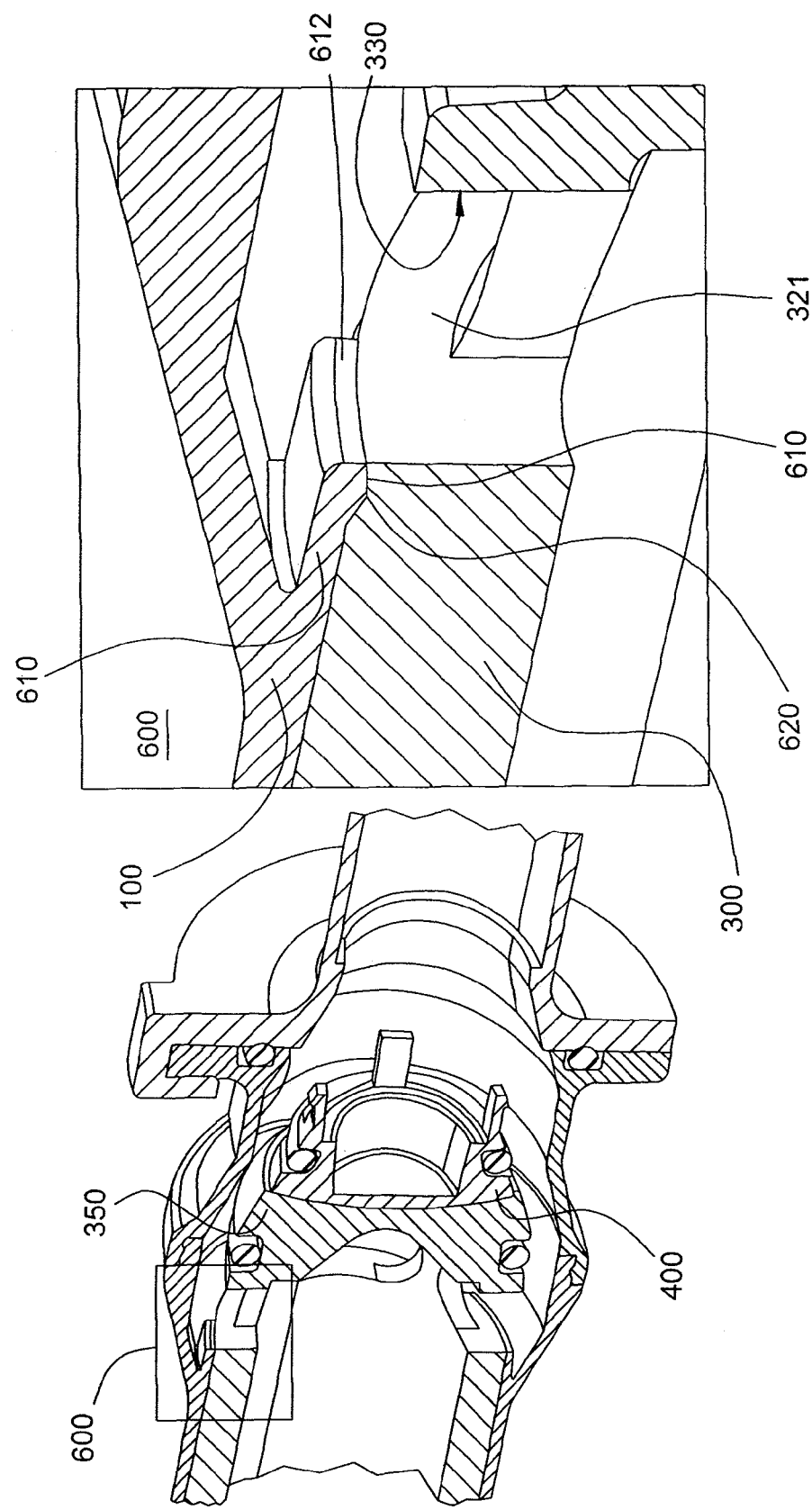

FIG. 24 is a partial perspective and cross-sectional view and an enlarged cross-sectional view of stem locking arrangement, preventing withdrawal of the stem from the first fitting.

Figure 25A:
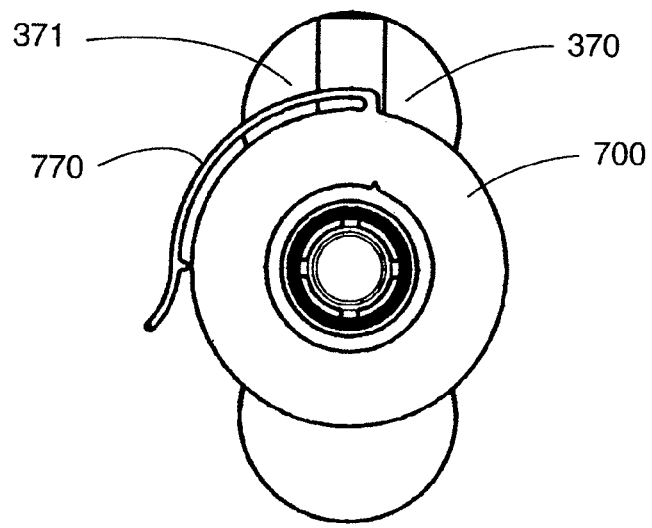
Figure 25B:
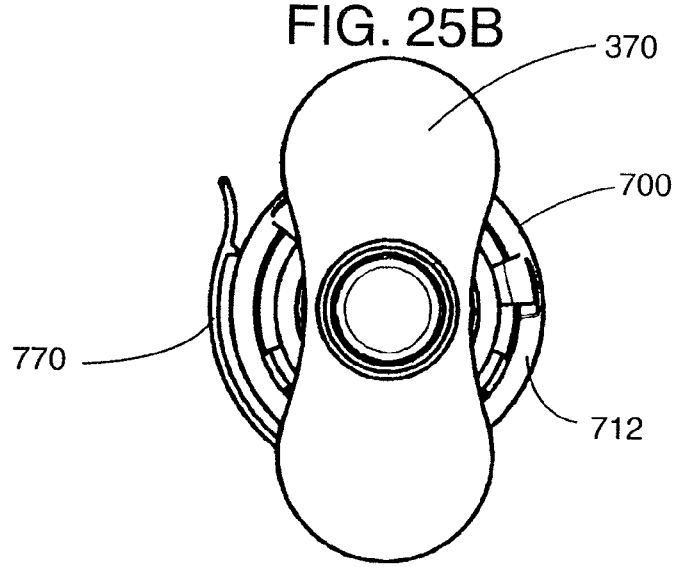
Figure 25C:
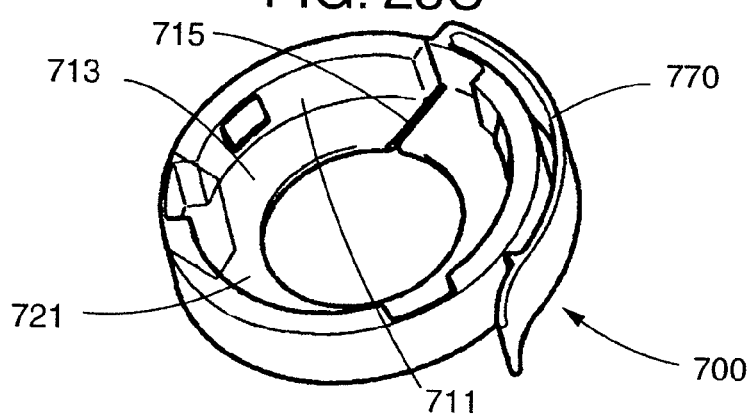

FIG. 25 is a first end view (FIG. 25A), a second end view (FIG. 25B) and a cut away sectional view (FIG. 25C) of a connection locking device, preventing separation of the first and second fittings.

Figure 26:
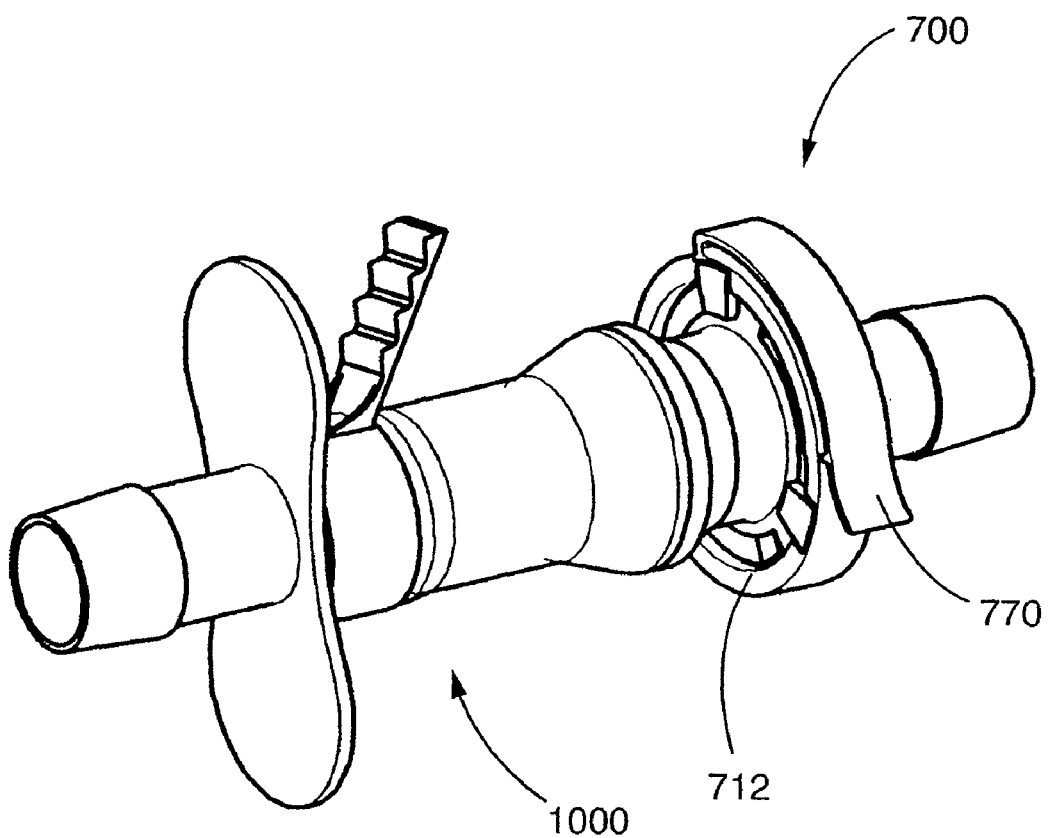

FIG. 26 is a perspective view of an embodiment of the assembly including the connection locking device shown in FIG. 25.

Figure 27A:
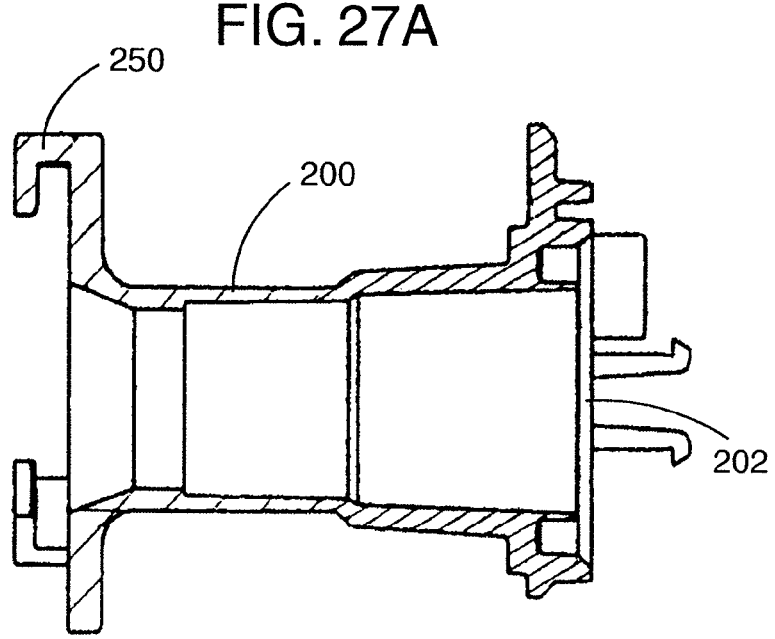
Figure 27B:
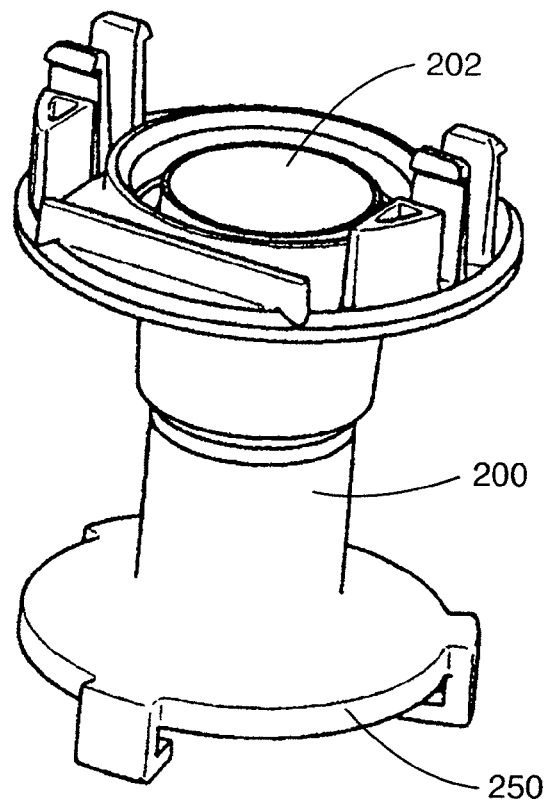

FIG. 27 shows one illustrative type of connector for embodiments of the assembly, wherein FIGS. 27A and 27B show cross-sectional and perspective views of a KLEEN-PAK® connector.

Figure 28A:
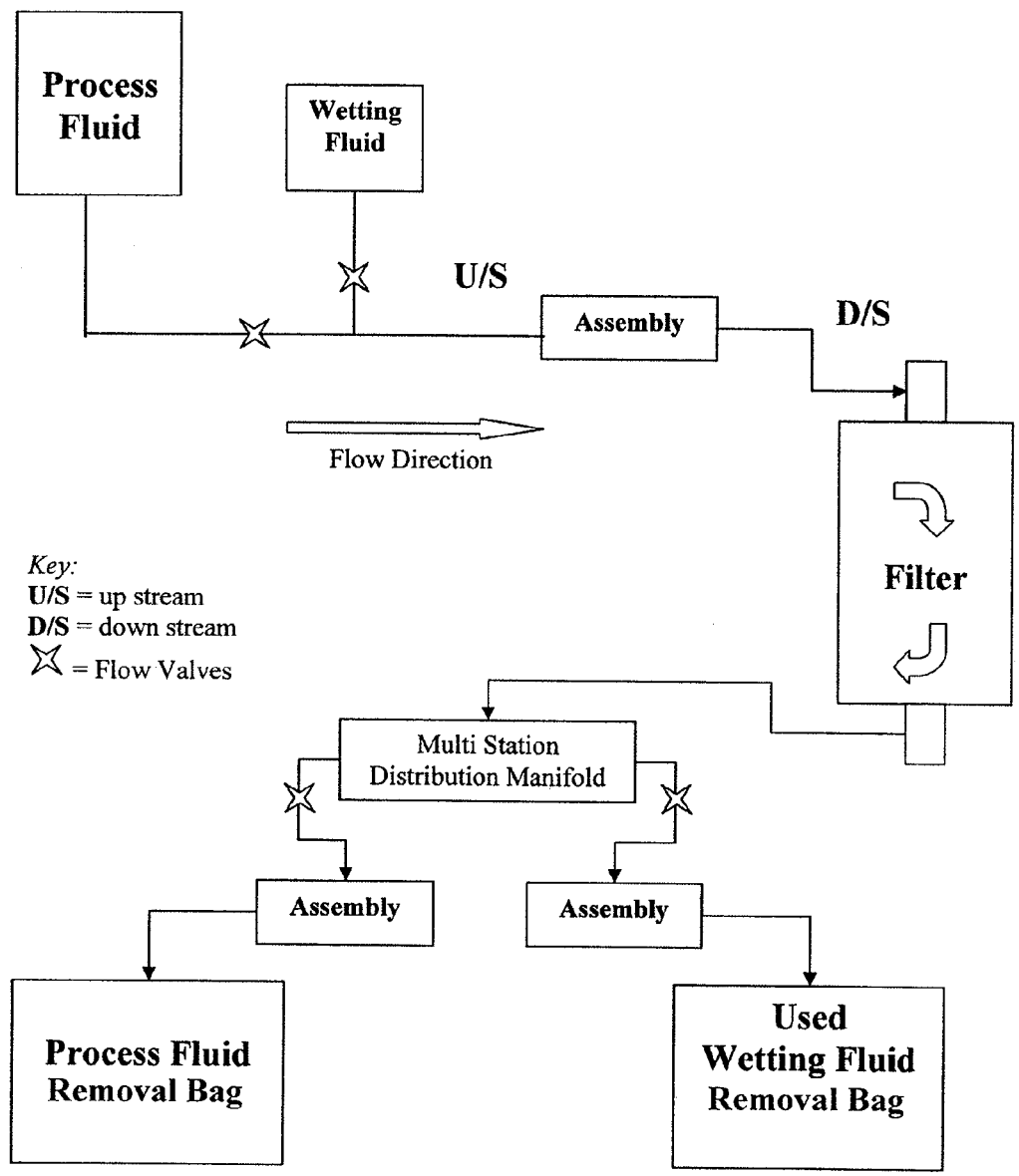
Figure 28B:
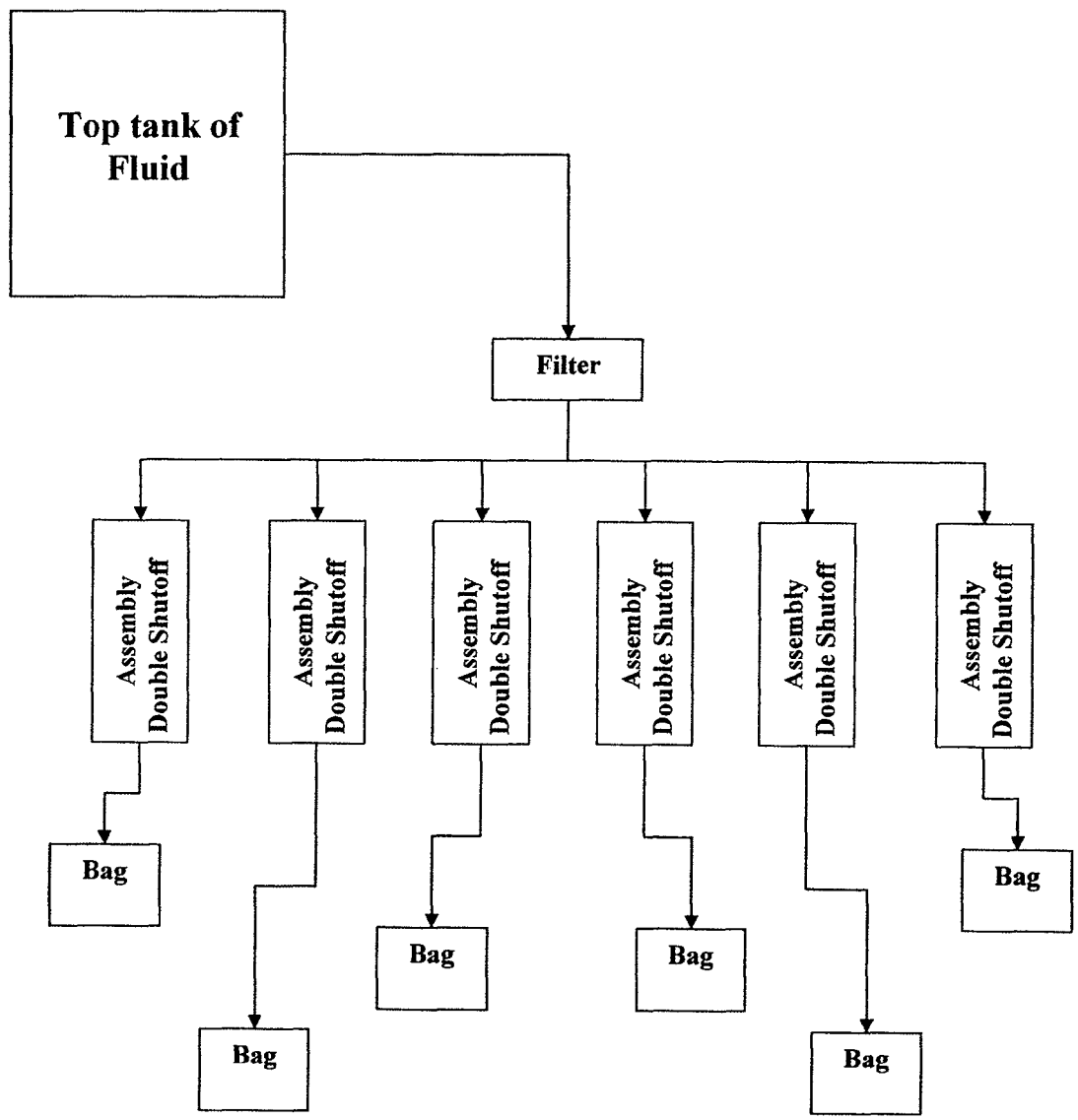

FIG. 28 (A and B) shows in schematic form, a plurality of illustrative embodiments of sets, each set including an assembly according to an embodiment of the invention, wherein the sets can be used in individually, or in combination.

DETAILED DESCRIPTION OF THE INVENTION

In an embodiment, a disconnectable connector assembly is provided comprising (a) a first polymeric fitting including a first open end, and a second open end; (b) a stem disposed in the first fitting, the stem including an open end and a closed end, a head comprising the closed end, a side wall including at least one aperture and two or more circumferential grooves, and at least two resilient members circumferentially engaging circumferential grooves in the side wall, wherein the stem is axially movable, from a first position to a second position, in the direction from the first end of the first fitting toward the second end of the first fitting; and, (c) a second polymeric fitting connected to the first fitting, the second fitting including a first end and a second end, the second fitting being in fluid communication with the stem and the first fitting when the stem is in the first position, and wherein fluid flow between the second fitting and the stem and the first fitting is blocked when the stem is in the second position; wherein the first fitting is disconnectable from the second fitting when the stem is in the second position.

In another embodiment, a disconnectable connector assembly comprises (a) a first polymeric fitting including a first open end, and a second open end; (b) a stem disposed in the first fitting, the stem including an open end and a closed end, a head comprising the closed end, a side wall including at least one aperture and at least two circumferential grooves, and at least two resilient members circumferentially engaging the side wall, wherein the stem is axially movable, from a first position to a second position, in the direction from the first end of the first fitting toward the second end of the first fitting; and, (c) a second polymeric fitting connected to the first fitting, the second fitting including a first end and a second end, the second fitting being in fluid communication with the first fitting when the stem is in the first position, and the stem blocks fluid flow between the first fitting and the second fitting when the stem is in the second position; wherein the first fitting is disconnectable from the second fitting when the stem is in the second position.

In accordance with an embodiment of the disconnection assembly according to the invention, the head of the stem is aligned with the second end of the first fitting when the stem is in the second position.

In an embodiment, the disconnection assembly further comprises a valve axially moveable by the stem, wherein the valve remains in the second fitting when the second fitting is disconnected from the first fitting. Preferably, the first end of the second fitting remain fluid tightly sealed when the first fitting is disconnected from the second fitting. In one embodiment, the valve is releasably attached to the stem, and the valve is released from the stem when the second fitting is disconnected from the first fitting. In another embodiment, the valve is not attached to the stem, for example, the assembly further comprises a valve guide and a spring in the second fitting, biasing the valve in an open position when the stem is in the first position.

In some embodiments wherein the disconnection assembly further comprises a valve, the valve includes a plurality of legs, and the second fitting comprises an inner sidewall comprising a lip, and the legs engage with the lip before the valve is released from the stem. The valve can be releasably attached to the stem, or the valve can be movably mounted in the second fitting.

In another embodiment, a set for processing fluid is provided comprising an embodiment of the disconnectable connector assembly, a first conduit attached to the open end of the stem; and, a second conduit attached to the second end of the second fitting. Embodiments of the set can include additional components, e.g., at least one container and/or at least one filter and/or at least one filter capsule, in fluid communication with the connector assembly.

A method for processing fluid according to an embodiment of the invention comprises passing the fluid through an embodiment of the disconnectable connector assembly; moving the stem from the first position to the second position; and disconnecting the first fitting from the second fitting.

In some embodiments, the method further comprises passing the fluid through a manifold before and/or after passing the fluid through the disconnectable filter assembly. Alternatively, or additionally, embodiments of the method comprise passing the fluid through a filter before passing the fluid through the disconnectable filter assembly.

In one embodiment of the method, the manifold includes at least a first port and a second port, wherein a first conduit and a first disconnectable filter assembly are in fluid communication with the first port, and a second conduit and a second disconnectable filter assembly are in fluid communication with the second port; and the method comprises passing a first portion of fluid through a first port and the first conduit and through the first disconnectable filter assembly, and disconnecting the first fitting from the second fitting of the first disconnectable filter assembly; and passing a second portion of fluid through a second port and through the second disconnectable filter assembly, and disconnecting the first fitting from the second fitting of the second disconnectable filter assembly.

A disconnectable connector assembly according to an embodiment of the invention includes mating fittings which can be coupled to connect different fluid processing components and/or different fluid conduit sections defining a fluid flow path, e.g., a liquid flow path. The assembly includes an axially moveable stem, wherein the fluid flow path can be open or closed depending on the position of the stem. The assembly isolates the fluid flow path from the ambient environment and from contaminants present in the ambient environment, and, after processing the fluid or fluids, the assembly can be disconnected while maintaining an aseptic seal where desired, without cutting tubing. Assemblies according to the embodiments of the invention can be used in open systems, and in closed systems.

Each fitting can be attached to or formed as part of any suitable conduit or fluid container, for example, a section of tubing, an inlet or outlet of a device such as a filter capsule, or a housing, e.g., a filter housing or drip chamber housing, or a container, e.g., flexible bag such as a blood bag. Each assembly comprises a structure that is suitable for fluid communication, preferably, liquid communication, e.g., a housing of any form capable of containing fluid. Preferably, the fittings and stem are formed from a polymeric material, e.g., molded from a polymeric material such as, for example, polycarbonate, polystyrene, polypropylene, or polysulfone. In some embodiments, the fittings are formed from a transparent or translucent polymeric material, e.g., to allow observation of the passage of fluid through the assembly.

In another embodiment, a set is provided, comprising at least one embodiment of the assembly, as well as conduits (tubing), e.g., a first conduit having one end attached to the open end of the stem, and a second conduit having one end attached to the second end of the second fitting; and, more preferably, at least one other component, such as at least one of any of the following, alone or in combination: a conduit, a container, a filter, and a filter capsule, wherein the assembly allows conduits to be disconnected while maintaining an aseptic seal where desired, without cutting tubing. In a typical embodiment of the set, at least one assembly is provided in an open position (stem in the first position), allowing fluid to pass through it, as part of a pre-manufactured and/or pre-assembled set. In some embodiments, the set includes at least two assemblies, and the set can include at least two different embodiments of the assembly, for example, the set can include an embodiment with a valve, and an embodiment without a valve, along with a plurality of conduits, and, if desired at least one other component, such as at least one of any of the following, alone or in combination: a conduit, a container, a filter, and a filter capsule.

For directional orientation in the following discussion, each fitting has a proximal end, nearest the opposing fitting, and a distal end furthest from the opposing fitting. Also, since the exemplary illustrated fittings and connectors comprise generally elongated bodies, the term axial denotes disposition along their axes.

The disconnectable connector assembly comprises first and second fittings, and a stem, wherein the stem is disposed in the first fitting, and is axially moveable therein from a first position to a second position. When the stem is in the first position, the assembly allows fluid to flow through the stem and the first fitting, and through the second fitting, or in the opposite direction. Subsequently, the stem is moved axially to a second position, preventing fluid flow from one fitting to another. The assembly is disconnectable when the stem is in the second position.

Each of the components of the invention will now be described in more detail below, wherein like components have like reference numbers.

In embodiments of the disconnection assembly illustrated in FIGS. 1, 7, and 16 (especially 1A, 7A, and 16), disconnection assembly 1000 comprises a first fitting 100 comprising a hollow body having opposite open ends (first open end 101 (distal end) and second open end 102 (proximal end)) and an interior passage 103 extending between the open ends and communicating with the ends. An axially moveable stem 300, having an interior passage 303, is telescopically housed in the first fitting 100. Before use, e.g., while manufacturing and/or assembling a set including an embodiment of the assembly, the first fitting 100 is connected to a second fitting 200. The second fitting 200 comprises a body having opposite ends (first open end 201 (proximal end) and second open end 202 (distal end)), and an interior passage 203 between the ends, wherein the passage communicates with the ends.

Figure 4A:
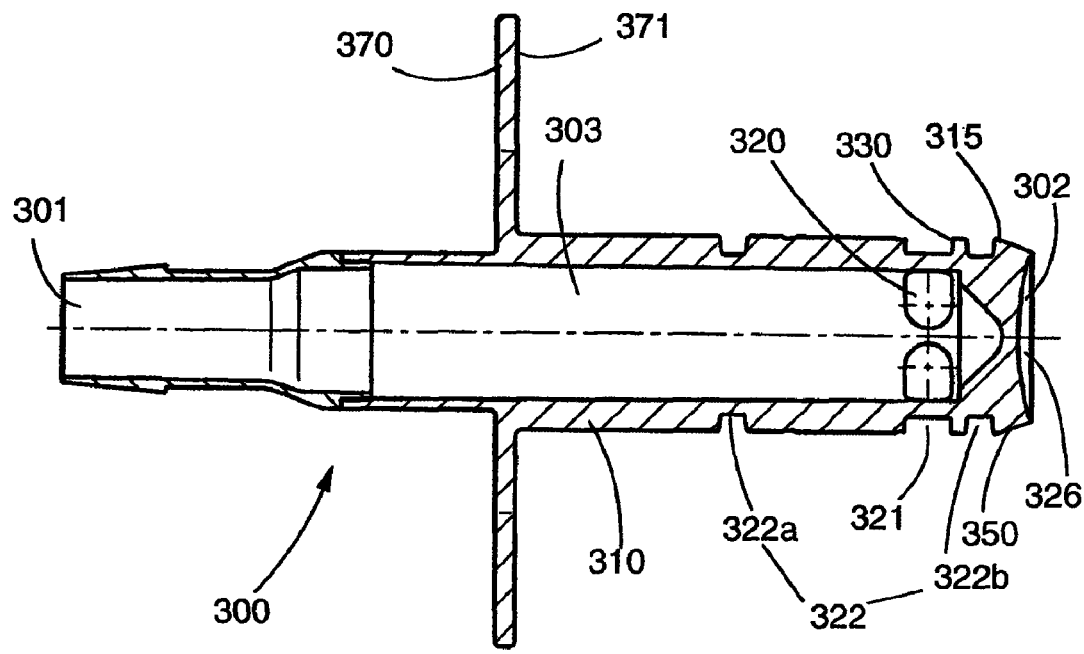
FIG. 4 shows a cross-sectional view (FIG. 4A) and a perspective view (FIG. 4B) of a stem used in the embodiment of the assembly shown in FIG. 1.

The stem 300, that is disposed in the first fitting and is axially moveable therein, comprises an open end 301 and a closed end 302, a side wall 310, and a head 350 comprising a sidewall 315 and the closed end, as illustrated in FIGS. 4A, 10, and 19 (wherein the illustrated embodiment of the stem shown in FIG. 4A is identical to the embodiment illustrated in FIG. 10). The stem has an interior passage 303 and the side wall 310 includes one or more apertures 320, preferably, two or more apertures 320 (in the illustrated embodiments, four apertures are shown in circumferential groove 321), providing a fluid flow path along the interior passage between the open end and the aperture(s). In the illustrated embodiments, the stem also comprises a handle 370, for ease in axially moving the stem.

Since the stem moves axially within the interior passage of the first fitting, the inner diameter of the first fitting is larger than the outer diameter of the stem. However, the inner diameter of the first fitting and the outer diameter of the stem are selected such that an aseptic fluid tight seal between the inner diameter of the first fitting and the outer diameter of the stem can be achieved along a desired portion or portions of the axial length of the assembly. The aseptic fluid tight seal is preferably provided using one or more resilient members (preferably o-rings) engaged with circumferential grooves, wherein the grooves are in the side walls of the stem and/or in the inner wall of the first fitting.

Figure 1A:
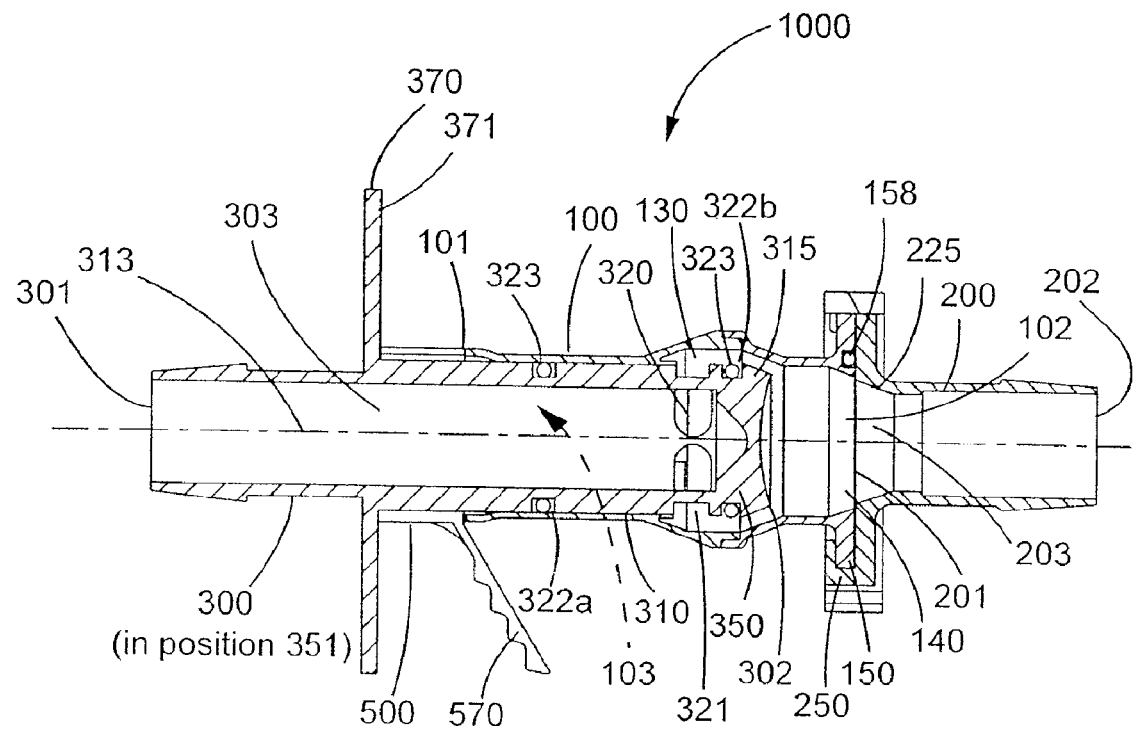
FIG. 1 shows a cross-sectional view (FIG. 1A) and a perspective view (FIG. 1B) of an embodiment of the disconnectable connector assembly of present invention comprising first and second fittings, and a stem, wherein the fittings are connected, and the stem is in the first position, allowing fluid flow through the assembly.
Figure 1B:
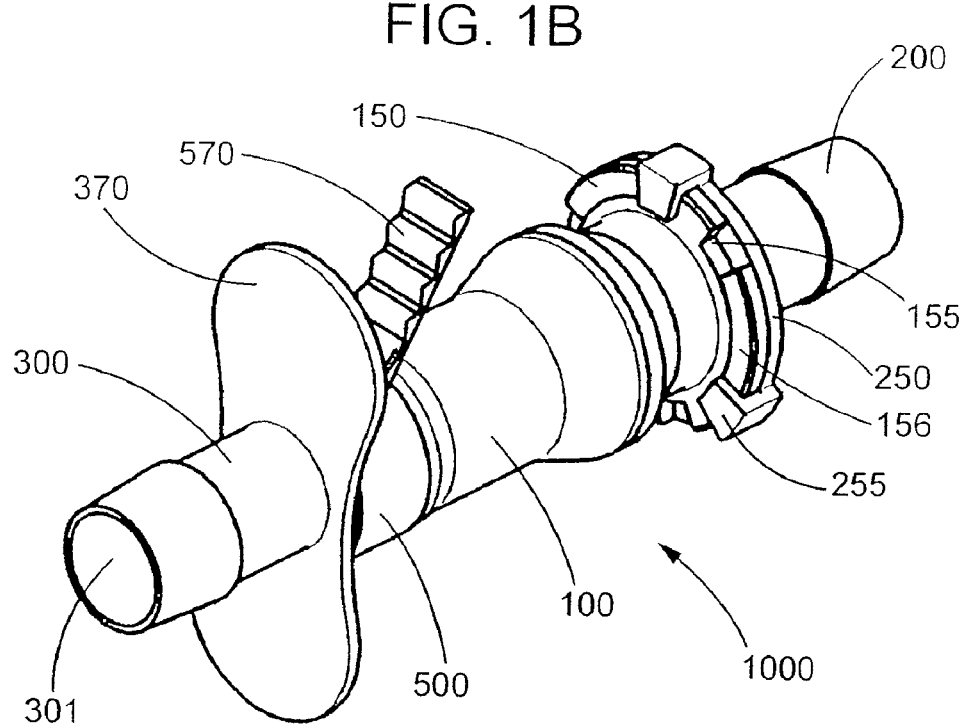
Figure 4B:
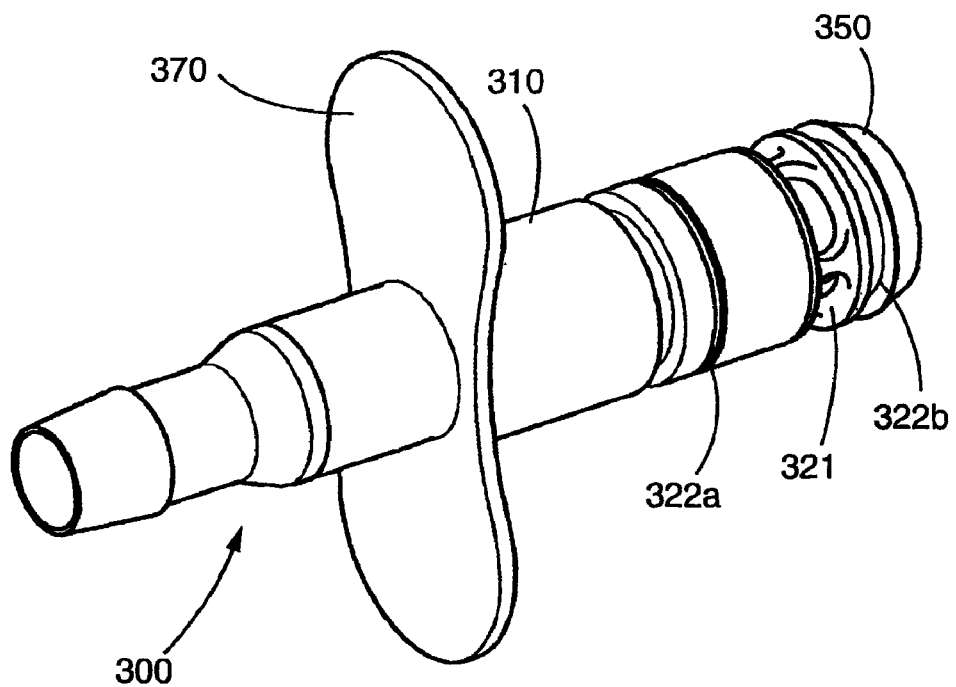

Typically, the side wall of the stem includes a plurality of spaced apart circumferential grooves, e.g., at least two axially spaced apart circumferential grooves, preferably, at least three axially spaced apart circumferential grooves and a separate resilient member engaging at least two of grooves, more preferably, wherein one groove is located in the side wall of the head, and another is located elsewhere in the sidewall of the body of the stem. Illustratively, in the embodiments shown in FIGS. 4 (A and B), 10, and 19, the side wall 310 of the stem has a plurality of axially spaced apart circumferential grooves 322 (first groove 322a, and second groove 322b), and, as shown in FIGS. 1A, 7A, and 16, a plurality of resilient members 323 circumferentially engaging these circumferential grooves and circumferentially engaging the side wall. Thus, in the illustrated embodiments, the resilient members each have an outer diameter greater than the outer diameter of the side wall of the stem, e.g., to provide a fluid tight seal between the resilient member engaged with the side wall of the stem, and the inner diameter of the first fitting, wherein a portion of the outer surface of the outer diameter of the resilient member or members sealingly and slidably engages the inner surface of the inner sidewall of the first fitting to provide the fluid tight seal.

Alternatively, or additionally, in another embodiment (not shown), the inner surface of the first fitting includes one or more circumferential grooves and one or more resilient members engaged with the grooves, and a portion of the inner surface of the inner diameter of the resilient member or members sealingly and slidably engages the outer surface of the stem to provide the fluid tight seal.

In accordance with embodiments of the invention, the stem can have any number of sidewall circumferential grooves and/or resilient members, and preferably has at least one sidewall circumferential groove wherein a resilient member does not engage the groove, e.g., as shown by circumferential groove 321 (including apertures 320) in FIGS. 1A, 7A, and 16. Preferably, the stem 300 includes circumferential groove 321 without a resilient member engaging the groove, wherein the groove is axially located between two other sidewall circumferential grooves 322a, 322b, and wherein the two other circumferential grooves (groove 322b in sidewall 315 of the head 350, and groove 322a in sidewall 310 of the body of the stem) each include a resilient member 323 engaged therein. More preferably, the groove without a resilient member is nearer to or adjacent the head of the stem than the groove is to the open end of the stem. In the illustrated embodiments (e.g., as shown in FIG. 4A), the groove 321 is adjacent the base of the head of the stem, bounded by surface 330.

Figure 5A:
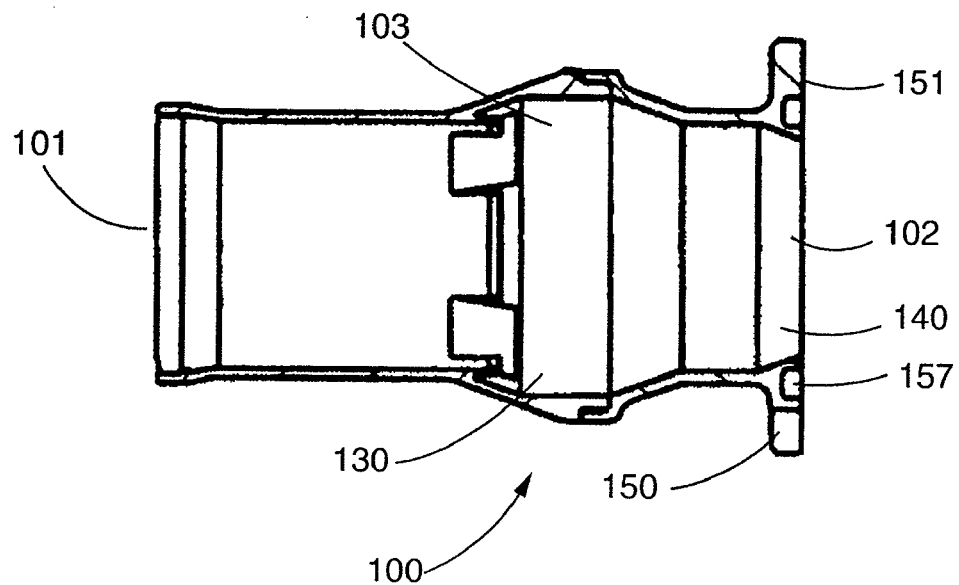
FIG. 5 shows a cross-sectional view (FIG. 5A) and a perspective view (FIG. 5B) of the first fitting shown in FIG. 1.

While a fluid tight seal between the stem and first fitting is provided along a desired portion or portions of the assembly, a section of the first fitting has an inner diameter larger than the outer diameter of the stem wherein fluid flow can occur between the outer diameter of the stem and the inner diameter of the fitting. Thus, as illustrated in FIG. 1A (and as shown in more detail in FIGS. 5A and 12, wherein the illustrated embodiment of the first fitting shown in FIG. 5A is identical to the embodiment illustrated in FIG. 12), the first fitting 100 has an enlarged inner diameter 130, for example, approaching the second end of the fitting, wherein the fitting also has a more narrow inner diameter 140, e.g., at the second end of the fitting 102. As will be noted in more detail below, fluid flow through the assembly can be allowed or prevented depending on the position of the stem.

The head 350 of the stem 300 can have a variety of configurations, e.g., having planar, non-planar and/or curved surfaces. For example, the surface 326 of the head 350 facing the second fitting can be a concave or substantially concave surface (e.g., in the embodiment shown in FIGS. 4A and 10), or it can be a flat or substantially flat, surface (e.g., in the embodiment shown in FIG. 19), or it can be a convex or substantially convex surface (not shown). In those embodiments wherein the assembly further comprises a valve, the configuration of the valve-contacting surface of the head is preferably selected for more efficient contact or mating with the stem-contacting surface of the valve, e.g., the opposing contacting surfaces of the head and valve can have substantially flat surfaces, the head can have a substantially concave surface and the valve can have a substantially convex surface, or the head can have a substantially convex surface and the valve can have a substantially concave surface. In one embodiment wherein a valve is releasably attached to the head (described in more detail below and as shown in FIG. 11), the surface of the head facing the valve has an annular undercut 327, for ease of releasable attachment to the valve.

Figure 2:
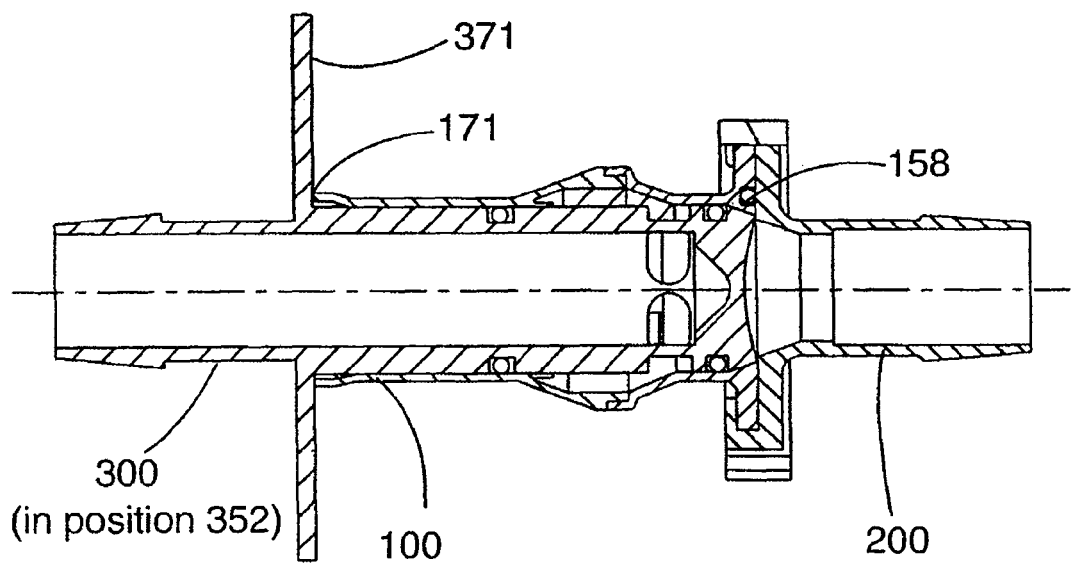
FIG. 2 is a cross-sectional view of the assembly shown in FIG. 1, wherein the stem is in the second position, preventing fluid flow through the assembly.
Figure 3:
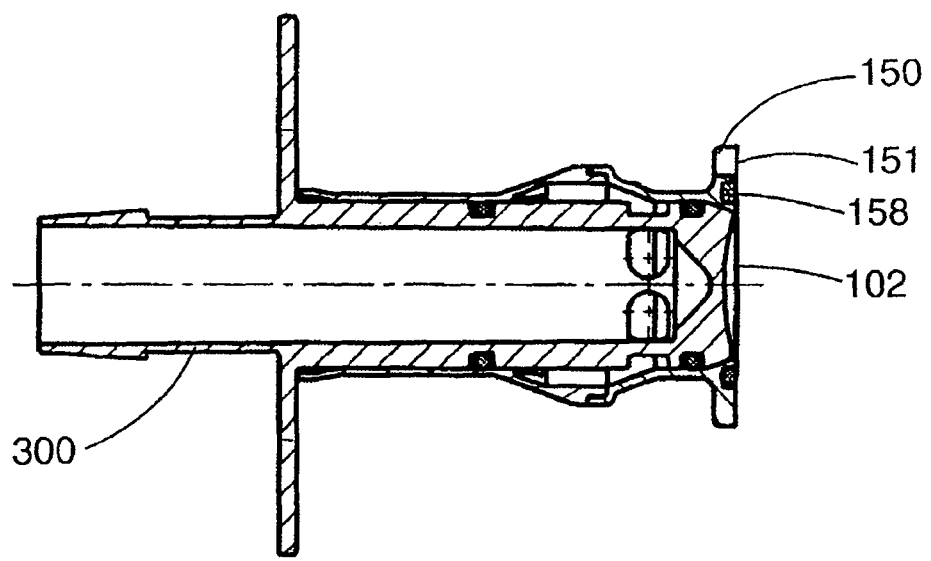
FIG. 3 is a cross-sectional view of the assembly shown in FIG. 1, after disconnection of the first fitting from the second fitting, showing the separated first fitting, wherein the stem is in the second position, and the disconnected end of the separated first fitting remains closed.
Figure 6A:
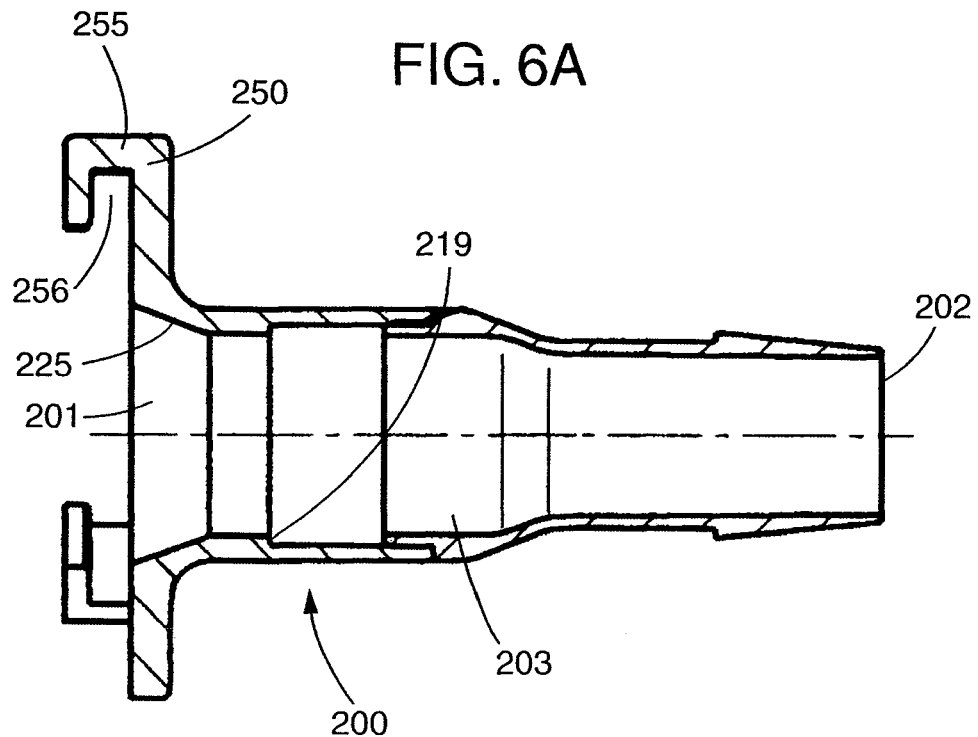
FIG. 6 shows a cross-sectional view (FIG. 6A) and a perspective view (FIG. 6B) of the second fitting shown in FIG. 1.

The second fitting 200 comprises a hollow body having opposite open ends (first end 201 (proximal end) and second end 202 (distal end)) and an interior passage 203 extending between, and communicating with, the ends, e.g., as shown in FIGS. 6A, 13, and 20 (wherein the illustrated embodiment of the second fitting shown in FIG. 6A is identical to the embodiment illustrated in FIG. 13). In accordance with the embodiments shown in FIGS. 1A, 7A, and 16, the first and second fittings 100, 200 are fluid tightly coupled together to allow fluid to pass through the stem 300 and first fitting and through the second fitting while the stem is in first position 351, wherein the head of the stem is positioned within the enlarged inner diameter 130 of the first fitting 100. When it is desired to stop the flow of fluid, or when flow has ceased, the stem is moved axially along the interior passage of the first fitting until the stem is in second position 352 (as shown in FIGS. 2, 8, and 17), wherein the head of the stem is positioned in narrower inner diameter 140 of the first fitting. When the stem is in second position 352, fluid flow through the stem and first fitting is blocked. If desired, the assembly can be configured, e.g., by selecting the length of the first fitting, so that the surface 371 of the handle 370 abuts the annular surface 171 at the end 100 of the first fitting, when the stem is in the second position.

The assembly 1000 is disconnectable (e.g., the second fitting 200 is disconnectable from the first fitting 100) when the stem 300 is in the second position 352. The first fitting remains fluid tightly sealed when the assembly is disconnected (e.g., the second end 102 of the first fitting remains fluid tightly sealed), and in some embodiments, the second fitting remains fluid tightly sealed (e.g., the first end 201 of the second fitting remains fluid tightly sealed) when the assembly is disconnected. While the second end of the first fitting, and in some embodiments, the first end of the second fitting, remain fluid tightly sealed when the fittings are disconnected, there may be a minor amount (e.g., $\leq$ about 0.01 ml) of residual fluid between the fittings, and thus, once disconnected, there may be slight spillage of this residual fluid.

A variety of configurations are suitable for allowing the second fitting to be connected to, and disconnected from, the first fitting. Suitable configurations for connection and disconnection of the first and second fittings include, for example, threaded connections, press-fit or friction-fit connections, luer connections, triclover connections, and twist connect/disconnect connections. Suitable configurations can include a combination of connection types.

Preferably, the assembly includes flanges providing for a twist connect/disconnect (e.g., the second end of the first fitting and the first end of the second fitting each further comprises a flange), wherein one fitting of the assembly comprises a flange comprising a face and one or more tabs and cut-outs, and the other fitting comprises a flange comprising a face and one or more fingers and slots, wherein, to provide connection, the fingers are inserted into the cut-outs, and upon twisting, one or more tabs engage with one or more slots (e.g., forming a tight friction fit) and the opposing faces are fluid tightly sealed when the assembly is connected. To provide disconnection, upon twisting (e.g., in the other direction than used for connection), the tabs are disengaged, and the second fitting is disconnected from the first fitting. In some embodiments, either or both flanges include one or more stops (e.g., preventing further twisting or making further twisting more difficult) when the flanges are twisted to make the connection.

In some embodiments, at least one fitting comprises a face includes a groove and a resilient member (preferably an o-ring) therein, the face being arranged to contact the face of the opposing fitting, e.g., to improve the fluid tight seal. Alternatively, or additionally, at least one fitting comprises a resilient portion molded (e.g., overmolded) to the face. For example, the resilient portion can be used rather than utilizing an o-ring. The resilient portion can be produced from the same material as the face, and, if desired, can be an integral portion of the face.

Figure 5B:
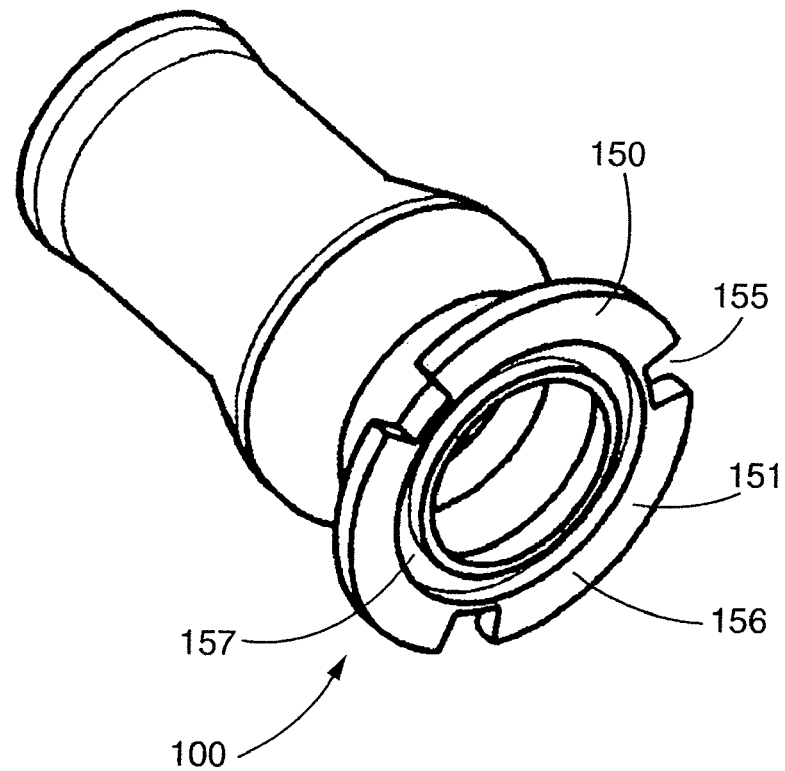
Figure 6B:
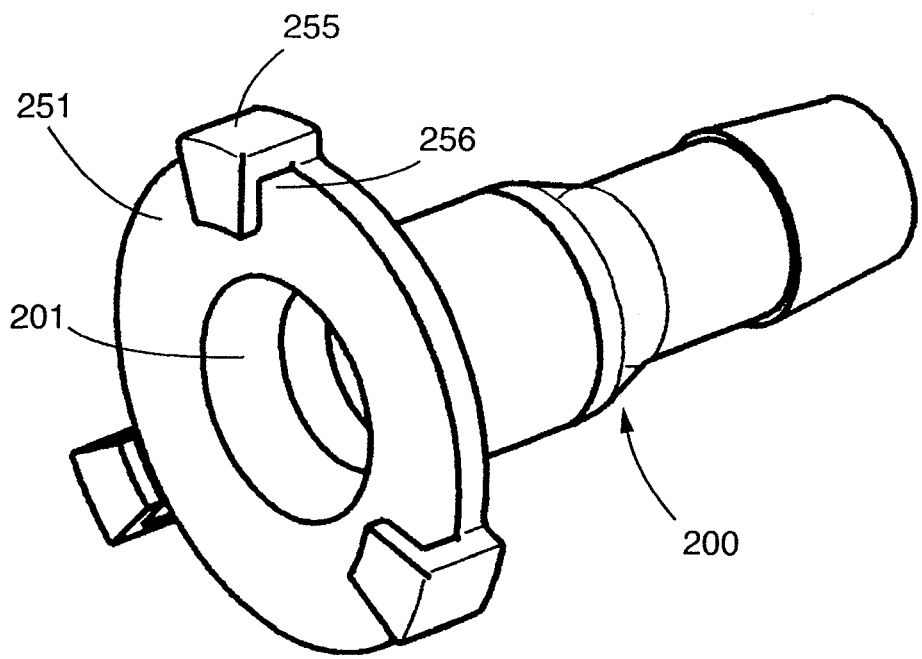

In accordance with the embodiments illustrated in FIGS. 5B and 6B, the first fitting 100 comprises flange 150 comprising face 151, cut-outs 155 (three cut-outs are illustrated), tabs 156 (three tabs are illustrated), and groove 157, suitable for receiving an o-ring (not shown), and the second fitting 200 comprises flange 250 comprising face 251, fingers 255 (three fingers are illustrated), and slots 256 (three slots are illustrated). During connection, fingers 255 are inserted into cut-outs 155, and one fitting is rotated, such that tabs 156 engage with the slots 256 of the fingers 255, and the o-ring and a portion of the face 151 sealingly contacts face 251. The procedure is reversed for disconnection of the fittings.

In some embodiments, e.g., as illustrated in FIGS. 7 (A and B) and 16, the assembly comprising first and second fittings and an axially moveable stem, further comprises a valve, which can be, for example, releasably attached to the head of the stem (FIG. 7, showing valve 400) or movably mounted in the second fitting (FIG. 16, showing valve 4400). In these embodiments, the head of the axially moving stem (moving toward the second position 352) moves the valve axially, until the valve is seated, and the valve is in the closed position (and the stem is in the second position), preventing flow through the second fitting.

In the embodiment illustrated in FIGS. 7-15, the valve 400 (shown in more detail in FIGS. 14A-C) comprises a head 450 comprising a stem-facing surface 426 and a sidewall 415. In some embodiments, e.g., as shown in FIGS. 7A and 11, the sidewall comprises a circumferential side wall groove 422, and the valve further comprises a resilient member 423 (e.g., an o-ring) engaged therein (FIGS. 14A and 14B show groove 422 without a resilient member engaged therein). Alternatively, or additionally, in some embodiments, e.g., as illustrated in FIG. 14C, the valve includes a circumferential resilient portion 424 (e.g., an overmold) in and/or on the side wall 415. For example, the resilient portion can be used rather than utilizing an o-ring. A variety of materials are suitable for producing the resilient portion, e.g., materials such as thermoplastic elastomers and silicon rubber.

Preferably, as shown in FIGS. 14A-B, the valve 400 includes a plurality of legs 411, e.g, two or more legs 411 (the illustrated embodiment has four legs), and, as shown in FIGS. 8, 13, and 15, the inner wall of the second fitting 200 includes a step or lip 219, wherein, when the valve is closed and seated, the surface 413 at the tips 412 of the legs 411 engage the step or lip 219, locking the valve in the closed position (as shown in more detail in FIG. 15). In this illustrated embodiment, the sidewall 415 of the head of the valve 400 has a beveled surface 425 and the end of the second fitting has a beveled surface 225 complementary to the bevel of the head, e.g., for a more efficient seal (in addition to the seal provided between the resilient member 423 and/or resilient portion 424 and the surface 225).

In accordance with the embodiment illustrated in FIG. 11, the head of the stem comprises a substantially concave surface 326 and an annular undercut 327, contacting the valve stem-facing surface 426 and a portion of the beveled surface 425 of the valve 400, allowing the valve to be releasably attached to the head of the stem. For example, the annular undercut 327 can include a groove or channel engaging a rib or protruberance on the sidewall of the valve 400. Once the valve 400 is seated in the second fitting (e.g., wherein the legs 411 engage the lip 219, as shown in FIG. 15), and upon separation of the second fitting 200 from the first fitting 100, the valve 400 is released from the stem 300, maintaining the fluid seal of the second end of the second fitting. Also, once the second fitting is separated from the first fitting, the head of the stem maintains the fluid seal of the second end of the first fitting.

Alternatively, in accordance with the embodiment illustrated in FIGS. 16-22, especially FIG. 20), the valve 4400 is moveably mounted to the second fitting 200. The valve is not attached to the head of the stem. In this illustrated embodiment, spring 4430 biases the valve 4400 in an open position until the head of the axially moving stem 350 (moving to the second position 352 as shown in FIG. 17) moves the valve axially, compressing the spring, until the valve is seated, and the valve is in the closed position (and the stem is in the second position), preventing flow through the second fitting.

In the embodiment illustrated in FIGS. 16-22, the valve 4400 (shown in more detail in FIGS. 20 and 22A) comprises a head 4450 comprising a stem-facing surface 4426 and a sidewall 4415. In the illustrated embodiments the sidewall comprises a circumferential side wall groove 4422, and the valve further comprises a resilient member 4423 (e.g., an o-ring) engaged therein. Alternatively, or additionally, in some embodiments (not shown), the valve includes a circumferential resilient portion (e.g., an overmold) in and/or on the side wall. A variety of materials are suitable for producing the resilient portion, e.g., materials such as thermoplastic elastomers and silicon rubber.

Preferably, as shown in FIGS. 16, 20, and 22A, the valve 4400 comprises a base 4428 comprising a plurality of legs 4411, e.g., two or more legs 4411 (the illustrated embodiment has four legs), and the inner wall of the second fitting 200 includes a step or lip 219 (shown in FIG. 20), wherein, when the valve is closed and seated, the surface 4413 at the tips 4412 of the legs 4411 engage the step or lip 219, locking the valve in the closed position. In the embodiment shown in FIGS. 20 and 22A, the sidewall 4415 of the head of the valve 4400 has a beveled surface 4425, and, as shown in FIG. 20, the end of the second fitting has a beveled surface 225 complementary to the bevel of the head, e.g., for a more efficient seal (in addition to the seal provided between the resilient member 4423 and/or the resilient portion, and the surface 225).

In the embodiments illustrated in FIGS. 20 and 22A, the valve 4400 further comprises a neck 4427 (between the head 4450 and the base 4428), and a chamber 4429 suitable for receiving the head of the spring 4430. As shown in FIG. 20, the illustrated spring 4430 comprises a head 4431, a biasing stem 4432, and a base 4433 comprising a platform 4434 and legs 4435, wherein the base sufficiently engages with the inner surface of the second fitting to prevent axial movement of the base.

The second fitting can include a device disposed in the fitting between the valve head and the valve base which guides and/or stabilizes the valve when the valve is axially advanced within the second fitting. For example, as shown in FIG. 21, an exemplary embodiment of the guide device 4448 includes a plurality of axially extending ribs 4449. The outer surface of the guide device can define a cylinder that has a diameter similar to the inner diameter of the second fitting 200 (e.g., to provide a friction fit between the outer surface of the device and the inner surface of the fitting), and the inner surfaces of the ribs can define an area that is similar to the outer area of the neck 4427 of the valve. Thus, when the head of the stem is advanced sufficiently to contact the head of the valve, and the valve moves axially in the second fitting, the inner surfaces of the ribs 4449 can contact the outer surface of the valve neck 4427 (or the inner surfaces of the ribs remain a small distance from the outer surface of the valve neck 4427), which guides and/or stabilizes the valve as it moves axially in the second fitting. Preferably, the guide device 4448 also retains the valve 4400 in the second fitting when the valve is in the open position (e.g., when the stem is in the first position 351). For example, using FIG. 20 for reference, when the spring 4430 biases the valve 4440 in the open position, surface 4448a of device 4448 (the surface facing the second end of the second fitting) contacts surface 4428a of base 4428 (the surface facing the first end of the second fitting), thus retaining the valve in the second fitting.

Typically, the assembly includes at least one lock-out device to prevent accidental or inadvertent axial advancement of the stem. The first fitting and/or stem can include the lock-out device. The lock-out device can have a variety of configurations, and typically comprises a deformable tab or tear strip, e.g., arranged to bend out of the way or break away from the stem and/or first fitting.

In the embodiment illustrated in FIGS. 1A, 1B, 23A and 23B, the lock-out device 500, surrounding a portion of the stem 300 and interposed between the handle 370 of the stem and the surface 171 at the first end of the first fitting, comprises a deformable tab 570, a substantially cylindrical body 510 having a side wall 511 including at least one frangible portion 512. The cylindrical body has an inner diameter larger than the outer diameter of the stem, and smaller than the outer diameter of the first fitting, wherein the tab can be easily grasped and bent, breaking the frangible portion and freeing the stem to move axially. In some embodiments (not shown), a plurality of lock-out devices can be included, e.g., a plurality of tabs, for example, wherein a portion of a first deformable tab abuts against a portion of a second deformable tab, that in turn has a portion that abuts against a portion of a third deformable tab, that in turn has a portion that abuts against the handle of the stem, preventing axial movement of the stem until the respective tab is broken away. For example, the first tab is broken away, and subsequently, the second and third deformable tabs are successively broken away, allowing further axial movement of the stem. Moreover, one or more tabs can be arranged to be broken away in a direction different from that of one or more other tabs, further ensuring that deliberate operator involvement is required in order to advance the stem axially only when desired. The use of the one or more tabs allows the desired axial movement of the stem to a desired position, e.g., allowing or preventing flow from the first fitting to the second fitting.

Alternatively, or additionally, the disconnection assembly can include a structure to prevent substantial retraction of the stem, e.g., the stem is not easily removable from the first fitting once the assembly is connected, and movement of the stem in the reverse direction is limited, so that the head can essentially only move toward the second fitting.

For example, the disconnection assembly can include a stem locking arrangement 600, e.g., as shown in FIG. 24, wherein one or more catches 610, coupled to the inner wall of the body of the first fitting, engage with corresponding depressions 620 in the outer surface of the stem before the stem is moved to the second position. The catches 610 each have a first face 611 and a second face 612. Preferably, the first face(s) 611 engage with the depression(s) 620 when the stem is in the first position. While the stem can be moved axially toward the second position, retraction of the stem will cause first face 611 to disengage from depression 620, and a portion of catch 610 will protrude into the open area of circumferential groove 321 in stem 300. Continued retraction of the stem will cause second face 612 to contact surface 330 of circumferential groove 321, and thus surface 330 provides a stop preventing further retraction of the stem. Additionally, the arrangement of resilient members providing a fluid tight seal between the stem and first fitting prevents fluid loss should attempts be made to retract the stem.

Alternatively, or additionally, the assembly can include a ratchet structure (not shown), such that the stem is not retractable once the head is advanced toward the second fitting, and the head can only move toward the second fitting. For example, the stem can include one or more ribs, preferably, a plurality of beveled annular ribs, circumfusing the external surface of the stem, wherein the ribs are beveled such that they project from the surface of the side wall of the stem, extending distally toward the handle, and forming an acute angle with the external surface of the stem. A catching member can be coupled to the inner wall of the body of the first fitting, wherein a distal end of the catching member includes a catch which rests on the outer surface of the stem. Accordingly, the engagement between the catch and angled rib allows advancement but prevents retraction of the stem.

In some embodiments of the invention, the disconnection assembly includes a connection locking device to prevent accidental or inadvertent disconnection, e.g., premature disconnection between the first and second fittings. For example, particularly for some embodiments wherein the disconnection device is provided assembled (e.g., as part of the pre-manufactured set, wherein the stem is in the first position) before use, the assembly can include a connection locking device such as a tear strip.

In the illustrative embodiment shown in FIGS. 25 (A-C) and 26, the assembly includes a connection locking device 700 comprising a substantially cylindrical body 710 having a handle 770, a side wall 711, a front wall 712, a rear wall 713, wherein the side wall as well as the front and/or rear wall includes at least one frangible portion 712, and an inner groove or channel 721, formed between the front and rear walls, the locking device being arranged around flanges of the first and second fittings, the inner groove or channel 721 having a width and diameter sufficient to accommodate the width and diameter of the flanges. When disconnection of the assembly is desired, the handle can be easily grasped and pulled or bent, breaking the frangible portion(s), and providing access to the flanges for disconnection.

Disconnection assemblies in accordance with embodiments of the invention can have a variety of connections for providing fluid communication with other components of, for example, one or more fluid processing systems or sets. For example, the first end of the stem and/or the second end of the second fitting can comprise threaded connectors, press-fit or friction-fit connectors, Luer connectors, triclover connectors, and twist connect/disconnect connectors (including, for example, the twist connect/disconnect connectors described above). In embodiment illustrated in FIG. 6B, the connector comprises a hose barb connector. The connectors can comprise, for example, and connectors and connector assemblies, including those disclosed in U.S. Pat. Nos. 5,393,101, 5,810, 398, and 6,655,655. In some embodiments, e.g., as illustrated in FIGS. 27A, and 27B, the connector(s) are suitable for use with, for example, KLEENPAK™ Connectors (Pall Corporation, East Hills, N.Y.).

Preferably, in accordance with embodiments of the invention, disconnection assemblies, and sets or systems including disconnection assemblies, are sterilized before use. The assemblies are compatible with a variety of sterilization protocols, including, for example, gamma sterilization and autoclaving.

Disconnection assemblies in accordance with embodiments of the invention can be placed in fluid communication with, for example, any suitable fluid container, housing, conduit and/or manifold. Illustratively, an end of a stem, fitting and/or connector can be bonded to, for example, a section of tubing, or to the top, bottom, or wall of a container, or to the inlet or outlet of a housing, using any suitable bonding technique (e.g., using an adhesive, a solvent, laser welding, radio frequency sealing, ultrasonic sealing and/or heat sealing). Additionally, or alternatively, the stem, fitting and/or connector may be injection molded to bond to the tubing, housing, or container. If desired, the stem, fitting and/or connector may be molded integrally with the tubing, housing, or container. In yet another embodiments, the stem, fitting and/or connector can provide a friction or push-on (e.g., barbed), threaded and/or clamped connection with the tubing, container, housing, and/or manifold.

The disconnection assemblies can be suitable for use in applications involving processing a wide variety of fluids, e.g., to transport one or more fluids, to separate one of more components from a fluid, to provide a desired solution and/or concentrate one or more desired components present in a fluid. For example, the assemblies can be suitable for applications involving treating process fluids such as fluids used in the biopharmaceutical industry, e.g., fluids including desirable components such as proteinaceous material, for example, peptides, enzymes, antibodies (e.g., monoclonal antibodies), or recombinant proteins such as growth factors. Other suitable process fluids include, for example, beverages, e.g., milk, beer and wine. Alternatively, or additionally, the disconnection assemblies can be used in transferring one or more of the following: buffer(s), cell culture medium or media, biological fluid(s), and pharmaceutical product(s), to a desired location.

A plurality of assemblies and/or sets including a plurality of assemblies can be utilized, e.g., as part of an overall process, in accordance with embodiments of the invention. For example, using the schematics shown in FIGS. 28A and B for reference (each Figure showing a plurality of illustrative sets), a process may include one or more of any of the following: priming a filter, filtering a process fluid, passing priming fluid and/or filtered process fluid through a manifold (e.g., a distribution manifold), passing the used priming fluid into a priming fluid container and passing a filtered process fluid into a process fluid container. Illustratively, an embodiment of the assembly can be used to provide fluid communication between the source containers of process fluid and priming fluid and the filter. Alternatively, or additionally, an embodiment of the assembly can be used to provide fluid communication between the manifold and the priming fluid container, and/or an embodiment of the assembly can be used to provide fluid communication between the manifold and the process fluid container. Some embodiments of the assembly may include a valve (e.g., identified in FIG. 28B as a "double shutoff" assembly), and some may not include a valve.

In some embodiments wherein it is desirable to obtain two or more samples (e.g., for analysis) of a fluid over a period of time, for example, once an hour, once a day, etc., it may be advantageous to maintain the sterility of the remaining fluid after taking the sample, without introducing contaminants into the sample, e.g., by utilizing an embodiment of the assembly including a valve. Illustratively (and using the schematic shown in FIG. 28B for reference), fluid from, for example, a fermentor or bioreactor can be passed to a manifold having a number of ports, wherein a plurality of ports communicate, via conduits and assemblies, with sampling containers, with an assembly including a valve (wherein the stem is initially in the first position) interposed between each port and respective container, and a flow control device, e.g., a conventional clamp, associated with each conduit leading from a port to an assembly. Before taking a sample, the clamp is initially closed. The clamp is subsequently opened, sample is passed into the sampling container, the stem is moved to the second position, and the first fitting is disconnected from the second fitting. If desired, the clamp can be closed after obtaining the sample and before moving the stem to the second position. This process can be repeated at subsequent ports, wherein samples are passed into the respective containers. Accordingly, sterility is maintained for the main batch of fluid, and the sampled fluid for analysis remains as it was when the sample was obtained.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A disconnectable connector assembly comprising:
  (a) a first polymeric fitting including a first open end, and a second open end;
  (b) a stem disposed in the first fitting, the stem including an open end and a closed end, a head comprising the closed end, a side wall including one or more apertures and a plurality of circumferential grooves, and a plurality of resilient members circumferentially engaging the circumferential grooves in the side wall, wherein the stem is axially movable, from a first position to a second position, in the direction from the first end of the first fitting toward the second end of the first fitting;
  (c) valve releasably attached to the stem, the valve including a plurality of legs, wherein the legs are engageable with a lip;
  (d) a second polymeric fitting connected to the first fitting, the second fitting including a first end and a second end, and the lip, the second fitting being in fluid communication with the stem and the first fitting when the stem is in the first position, and wherein fluid flow between the second fitting and the stem and the first fitting is blocked when the stem is in the second position;
    wherein the first fitting is disconnectable from the second fitting when the stem is in the second position and the valve is released from the stem and remains in the second fitting with the legs of the valve engaged with the lip, sealing the valve in the first end of the second fitting, when the first and second fittings are disconnected; and, (e) the assembly further comprises one or more of the following (i)-(iii):
  (i) a stem locking arrangement comprising at least one depression in the side wall of the stem, and a catch engageable with the depression, wherein the first fitting includes the catch;
  (ii) a lock-out device comprising a deformable tab having a frangible portion, the device preventing axial movement of the stem until the device is removed; and
  (iii) a connection locking device comprising a substantially cylindrical body, a handle, and at least one frangible portion, the locking device preventing disconnection of the first fitting from the second fitting until the locking device is removed.

2. The assembly of claim 1, wherein the stem includes at least first, second, and third circumferential grooves along the axial length of the stem, wherein the head includes the first circumferential groove, and the assembly includes first and second resilient members, the first resilient member engaging the first circumferential groove, and the second resilient member engaging the second circumferential groove; wherein the third circumferential groove is between the first and second circumferential grooves, and the third circumferential groove includes at least two apertures.

3. The assembly of claim 1, wherein the second end of the first fitting and the first end of the second fitting each further comprise a flange, and the flanges are connectable to each other, and disconnectable from each other.

4. The assembly of claim 1, wherein the open end of the stem further comprises a first connector and the second end of the second fitting further comprises a second connector.

5. The assembly of claim 1, wherein the side wall of the stem includes a plurality of apertures.

6. The assembly of claim 1, wherein the first connector and/or the second connector comprise barbed connectors.

7. The assembly of claim 1, wherein the first connector and/or the second connector comprise flanges.

8. A set for processing fluid comprising:
  the disconnectable connector assembly of claim 1;
  a first conduit attached to the open end of the stem; and, a second conduit attached to the second end of the second fitting.

9. The set according to claim 8, further comprising a container in fluid communication with the second conduit.

10. The set according to claim 9, further comprising an additional container in fluid communication with the first conduit.

11. The set according to claim 8, further comprising a container in fluid communication with the first conduit.

12. A method for processing fluid comprising:
  passing the fluid through the disconnectable connector assembly of claim 1; moving the stem from the first position to the second position; and disconnecting the first fitting from the second fitting.

13. The method of claim 12, including passing the fluid through a manifold before passing the fluid through the disconnectable connector assembly and disconnecting the first fitting from the second fitting.

14. The method of claim 13, wherein the manifold includes at least a first port and a second port, wherein a first conduit and a first disconnectable connector assembly are in fluid communication with the first port, and a second conduit and a second disconnectable connector assembly are in fluid communication with the second port; and the method comprises
  passing a first portion of fluid through the first port and the first conduit and through the first disconnectable connector assembly, and disconnecting the first fitting from the second fitting of the first disconnectable connector assembly; and,
  passing a second portion of fluid through a second port and through the second disconnectable connector assembly, and disconnecting the first fitting from the second fitting of the second disconnectable connector assembly.

15. The method of claim 12, including passing the fluid through a filter before passing the fluid through the disconnectable connector assembly and disconnecting the first fitting from the second fitting.

16. The disconnectable connector assembly of claim 1, comprising at least two of: (i), (ii) and (iii).

17. A set for processing fluid comprising:
  the disconnectable connector assembly of 16;
  a first conduit attached to the open end of the stem; and, a second conduit attached to the second end of the second fitting.

18. The &connectable connector assembly of claim 1, comprising (i), (ii) and (iii).

19. A set for processing fluid comprising:
  the disconnectable connector assembly of 18;
  a first conduit attached to the open end of the stem; and, a second conduit attached to the second end of the second fitting.

* * * * *